(12) United States Patent
Lotz et al.

(10) Patent No.: US 7,671,225 B2
(45) Date of Patent: Mar. 2, 2010

(54) FERROCENYL LIGANDS FOR HOMOGENEOUS, ENANTIOSELECTIVE HYDROGENATION CATALYSTS

(75) Inventors: Matthias Lotz, Basel (CH); Felix Spindler, Starrkirch-Wil (CH)

(73) Assignee: Umicore AG & Co. KG, Hanau-Wolfgang (DE)

( * ) Notice: Subject to any disclaimer, the term of this patent is extended or adjusted under 35 U.S.C. 154(b) by 513 days.

(21) Appl. No.: 11/579,692

(22) PCT Filed: May 3, 2005

(86) PCT No.: PCT/EP2005/052009
§ 371 (c)(1),
(2), (4) Date: Nov. 6, 2006

(87) PCT Pub. No.: WO2005/108409
PCT Pub. Date: Nov. 17, 2005

(65) Prior Publication Data
US 2008/0287698 A1    Nov. 20, 2008

(30) Foreign Application Priority Data
May 7, 2004   (CH)   ..................... 0811/04

(51) Int. Cl.
*C07F 19/00* (2006.01)
*C07F 17/02* (2006.01)
(52) U.S. Cl. .............. 556/28; 556/14; 556/21; 556/144; 987/33; 987/37
(58) Field of Classification Search .................. 556/14, 556/21, 28, 144; 987/33, 37
See application file for complete search history.

(56) References Cited
U.S. PATENT DOCUMENTS

| | | | |
|---|---|---|---|
| 6,191,284 B1 | 2/2001 | Knochel et al. | |
| 7,015,342 B2 * | 3/2006 | Knochel et al. | ............... 556/14 |
| 7,435,840 B2 * | 10/2008 | Pfaltz et al. | .................. 556/16 |
| 2005/0240007 A1 | 10/2005 | Knochel et al. | |

FOREIGN PATENT DOCUMENTS

DE    102 19 490    11/2003

\* cited by examiner

*Primary Examiner*—Porfirio Nazario Gonzalez
(74) *Attorney, Agent, or Firm*—Wenderoth, Lind & Ponack, L.L.P.

(57) ABSTRACT

Compounds of the formula (I) or (I'), where $R_1$ is a hydrogen atom or $C_1$-$C_4$-alkyl and $R'_1$ is $C_1$-$C_4$-alkyl; $X_1$ and $X_2$ are each, independently of one another, a secondary phosphine group; $R_2$ is hydrogen, $R_{01}R_{02}R_{03}Si$—, $C_1$-$C_{18}$.acyl substituted by halogen, hydroxy, $C_1$-$C_8$-alkoxy or $R_{04}R_{05}N$—, -or $R_{06}$—$X_{01}$—C(O)—; $R_{01}$, $R_{02}$ and $R_{03}$ are each, independently of one another, $C_1$-$C_{12}$-alkyl, unsubstituted or $C_1$-$C_4$-alkyl or $C_1$-$C_4$-alkoxy-substituted $C_6$-$C_{10}$-aryl or $C_7$-$C_{12}$-aralkyl; $R_{04}$ and $R_{05}$ are each, independently of one another, hydrogen, $C_1$-$C_{12}$-alkyl, $C_3$-$C_8$-cycloalkyl, $C_6$-$C_{10}$-aryl or $C_7$-$C_{12}$-aralkyl, or $R_{04}$ and $R_{05}$ together are trimethylene, tetramethylene, pentamethylene or 3-oxapentylene; $R_{06}$ is $C_1$-$C_{18}$-alkyl, unsubstituted or $C_1$-$C_4$-alkyl- or $C_1$-$C_4$-alkoxy-substituted $C_3$-$C_8$-cycloalkyl, $C_6$-$C_{10}$-aryl or $C_7$-$C_{12}$-aralkyl; $X_{01}$ is —O— or —NH—; T is $C_6$-$C_{20}$-arylene; v is 0 or an integer from 1 to 4; and \* denotes a mixture of racemic or enantiomerically pure diastereomers or pure racemic or enantiomerically diastereomers, are excellent chiral ligands for metal complexes as enantioselective catalysts for the hydrogenation of prochiral organic compounds.

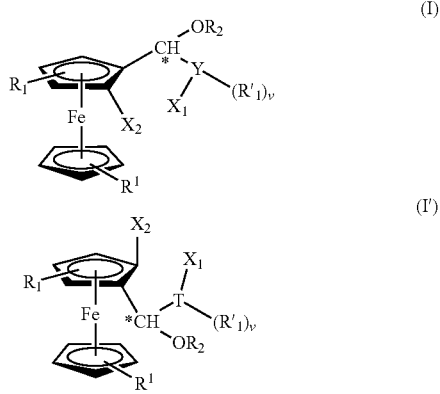

31 Claims, No Drawings

FERROCENYL LIGANDS FOR HOMOGENEOUS, ENANTIOSELECTIVE HYDROGENATION CATALYSTS

The present invention relates to 1-secondary-phosphino-2-[(2'-secondary-phosphino-C aromat-1'-yl)hydroxymethyl]ferrocenes as ligands for metal complexes, metal complexes of transition metals and these ligands, and the use of the metal complexes for the enantio-selective hydrogenation of prochiral, organic, unsaturated compounds having at least one carbon-carbon or heteroatom-carbon double bond.

Chiral diphosphines have proven to be valuable ligands for catalytically active metal complexes used in homogeneous catalyses for the enantioselective hydrogenation of prochiral, organic compounds to prepare intermediates for active compounds or to prepare active compounds directly, for example pharmaceuticals, pesticides or aromas including fragrances. Over the course of time, many studies have shown that the effectiveness of the catalysts in respect of optical selectivity, activity and conversion depends on the ligands and for the same substrate can vary more or less greatly depending on the ligand. It cannot be predicted which ligands give optimum results for a particular substrate. For this reason, it continues to be desirable to provide new ligands so as to provide a broad range from which it is possible to select ligands which enable most optimal conditions for a hydrogenation to be achieved for particular substrates.

Among diphosphines having a ferrocene skeleton, 1-secondary-phosphino-2-(2'-secondary-phosphino-1'-benzyl) ferrocenes, for example, have proven to be valuable ligands for rhodium complexes for the enantioselective hydrogenation of prochiral, ethylenically unsaturated compounds. They have the trivial name TANIAPHOS and are described in WO 00/37478. The methylene group of the benzyl radical can, for example, be substituted by alkoxy or acyloxy. Substitution of the methylene group by hydroxyl is not described nor is a synthetic route which could lead to hydroxyl-substituted ligands described. WO 03/093285 describes 1-secondary-phosphino-2-[(2'-secondary-phosphinophen-1'-yl)-$C_1$-$C_4$-alkoxy-methyl]ferrocenes in the form of diastereomers, with the mixture of strereoisomers being enriched in particular enantiomers. These compounds are obtained by replacement of a sulphoxide radical as chiral auxiliary group by a monohalophosphine in the presence of a strong lithium base, with hydroxybenzyl intermediates formed by addition of 1-secondary-phosphinobenzaldehyde onto the ferrocene sulphoxide being converted into the alkoxy derivatives beforehand.

Although enriched mixtures of enantiomers were prepared by the method described in WO 03/093285, no hydroxyl-substituted derivatives have been prepared in this way. In Chirals CHIMICA OGGI/chemistry today (2000), pages 48 to 52, A. Börner states that the presence of hydroxyl groups in diphosphine ligands can influence the catalytic properties of metal complexes in respect of conversion and optical selectivity.

In ferrocenes, metallation generates planar chirality. It has now been found that 1-secondary-phosphino-2-[(2'-secondary-phosphinophen-1'-yl)hydroxymethyl]ferrocenes are obtained in high yields and even, possibly, by means of simple chromatographic separation, in the form of pure enantiomers if a ferrocene having a chiral diaminophosphine group is firstly diastereoselectively metallated in the ortho position and then reacted with an ortho-secondary-phosphinobenzaldehyde or ortho-halobenzaldehyde. At this stage, the enantiomers can, if necessary, be separated in a simple manner by known methods. The further reaction to form the desired diphosphines can then be carried out in a manner known per se. Surprisingly, it has also been found that a high catalytic activity and very high optical yields comparable to the results obtained when using metal complexes having methoxy ligands are achieved in the hydrogenation of prochiral olefins using metal complexes of the hydroxy ligands. In addition, it has surprisingly been found that significantly higher optical yields are achieved in the hydrogenation of prochiral heteroatom-carbon double bonds, for example carbonyl groups, when using hydroxy ligands. A further advantage of the hydroxy ligands is that the hydroxyl group can easily be alkylated or acylated to produce known ligands.

The invention firstly provides compounds of the formula I or I',

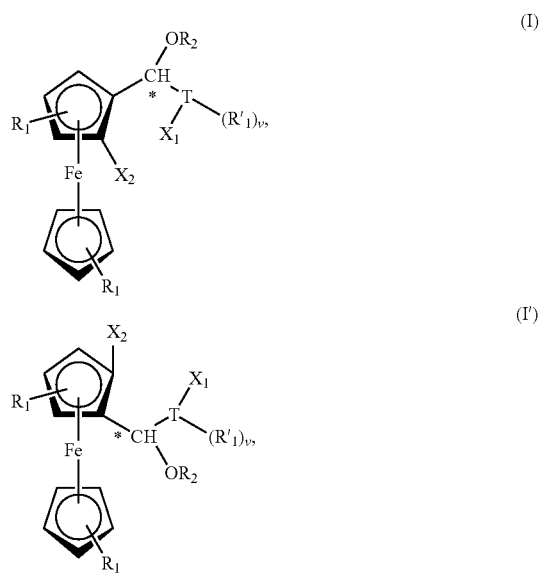

where
both $R_1$ are independently a hydrogen atom or $C_1$-$C_4$-alkyl and $R'_1$ is $C_1$-$C_4$-alkyl;
$X_1$ and $X_2$ are each, independently of one another, a secondary phosphine group;
$R_2$ is hydrogen, $R_{01}R_{02}R_{03}Si$—, $C_1$-$C_{18}$-acyl substituted by halogen, hydroxy, $C_1$-$C_8$-alkoxy or $R_{04}R_{05}N$—, or $R_{06}$—$X_{01}$—$C(O)$—;
$R_{01}$, $R_{02}$ and $R_{03}$ are each, independently of one another, $C_1$-$C_{12}$-alkyl, unsubstituted or $C_1$-$C_4$-alkyl- or $C_1$-$C_4$-alkoxy-substituted $C_6$-$C_{10}$-aryl or $C_7$-$C_{12}$-aralkyl;
$R_{04}$ and $R_{05}$ are each, independently of one another, hydrogen, $C_1$-$C_{12}$-alkyl, $C_3$-$C_8$-cycloalkyl, $C_6$-$C_{10}$-aryl or $C_7$-$C_{12}$-aralkyl, or $R_{04}$ and $R_{05}$ together are trimethylene, tetramethylene, pentamethylene or 3-oxapentylene;
$R_{06}$ is $C_1$-$C_{18}$-alkyl, unsubstituted or $C_1$-$C_4$-alkyl- or $C_1$-$C_4$-alkoxy-substituted $C_3$-$C_8$-cycloalkyl, $C_6$-$C_{10}$-aryl or $C_7$-$C_{12}$-aralkyl;
$X_{01}$ is —O— or —NH—;
T is $C_6$-$C_{20}$-arylene;
v is 0 or an integer from 1 to 4;
$X_1$ is bound in the ortho position relative to the T-C* bond; and
* denotes a mixture of racemic or enantiomerically pure diastereomers or pure racemic or enantiomerically pure diastereomers.

Preferred compounds according to the invention are compounds of the formula Ia or Ib,

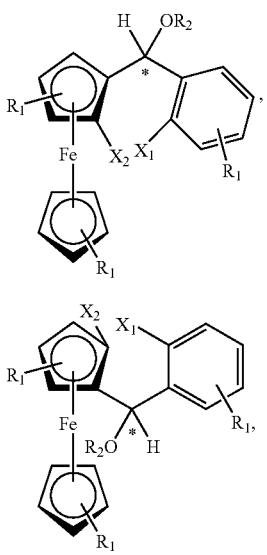

where $R_1$, $X_1$, $X_2$ and $R_2$ and * have the meanings indicated above.

$R_1$ can be present from one to three times or from one to five times in the cyclopentadienyl rings. An alkyl group $R_1$ can be, for example, methyl, ethyl, n- or i-propyl, n-, i- or t-butyl, with methyl being preferred. $R_1$ is preferably a hydrogen atom.

In a preferred embodiment, $R_2$ is a hydrogen atom.

Alkyl groups $R_{01}$, $R_{02}$ and $R_{03}$ can be linear or branched and the alkyl preferably has from 1 to 8 carbon atoms, particularly preferably from 1 to 4 carbon atoms. Aryl groups $R_{01}$, $R_{02}$ and $R_{03}$ can be, for example, phenyl or naphthyl and aralkyl groups $R_{01}$, $R_{02}$ and $R_{03}$ can be benzyl or phenylethyl. Some examples of $R_{01}$, $R_{02}$ and $R_{03}$ are methyl, ethyl, n- or i-propyl, n-, i- or t-butyl, pentyl, hexyl, heptyl, octyl, nonyl, decyl, undecyl, dodecyl, phenyl, benzyl, methylphenyl, methylbenzyl, methoxyphenyl, dimethoxyphenyl and methoxybenzyl. Some preferred examples of silyl groups $R_{01}R_{02}R_{03}Si$— are trimethylsilyl, tri-n-butylsilyl, t-butyldimethylsilyl, 2,2,4,4,-tetramethylbut-4-yl-yldimethylsilyl and triphenylsilyl.

In a preferred embodiment, $R_{04}$ and $R_{06}$ are each, independently of one another, hydrogen, $C_1$-$C_4$-alkyl, $C_5$-$C_6$-cycloalkyl, phenyl or benzyl, or $R_{04}$ and $R_{05}$ together are tetramethylene, pentamethylene or 3-oxapentyl-1,5-ene. The substituent $C_1$-$C_8$-alkoxy is preferably $C_1$-$C_4$-alkoxy such as methoxy, ethoxy, propoxy or butoxy.

An acyl group $R_2$ preferably has from 1 to 12 carbon atoms, particularly preferably from 1 to 8 carbon atoms, and is, in particular, derived from a carboxylic acid. Examples of such carboxylic acids are aliphatic, cycloaliphatic and aromatic carboxylic acids having from 1 to 18 carbon atoms, preferably from 1 to 12 carbon atoms. Some examples of substituted acyl are phenylsulphonyl, toluenesulphonyl, methylsulphonyl, phenylphosphonyl, acetyl, propanoyl, butanoyl, pentanoyl, hexanoyl, octanoyl, dodecanoyl, tetradecanoyl, octadec-anoyl, cyclohexylcarbonyl, benzoyl, methylbenzoyl, phenylacetyl, pyridylcarbonyl, naphthyl-carbonyl. Some examples of substituted acyl are groups of the formula $R_{07}$—C(O)—, where $R_{07}$ is hydroxymethyl, methoxymethyl, ethoxymethyl, 2-hydroxyeth-1-yl, 2-methoxyeth-1-yl, hydroxypropanoyl, fluoromethyl, chloromethyl, difluoromethyl, dichloromethyl, trifluoro-methyl, trichloromethyl, aminomethyl, methylaminomethyl, dimethylaminomethyl, 1-amino-eth-1-yl, 1-methylaminoeth-1-yl, 1-dimethylaminoeth-1-yl, 2-aminoeth-1-yl, 3-aminoprop-1-yl, 4-aminobut-1-yl, pyrrolinyl-N-methyl, piperidinyl-N-methyl, morpholino-N-methyl, 4-amino-cyclohex-1-yl, methoxyphenyl, hydroxyphenyl, aminophenyl, dimethylaminophenyl, hydroxy-benzyl, p-aminobenzyl and p-dimethylaminobenzyl.

An alkyl group $R_{06}$ has from 1 to 12 carbon atoms, particularly preferably from 1 to 8 carbon atoms. The alkyl can be linear or branched. A cycloalkyl group $R_{06}$ is preferably cyclopentyl or cyclohexyl. An aryl group $R_{06}$ can be naphthyl or in particular phenyl. An aralkyl group $R_{06}$ can be phenylethyl or in particular benzyl. Some examples of $R_{06}$ are methyl, ethyl, n- or i-propyl, n-, i- or t-butyl, pentyl, hexyl, heptyl, octyl, nonyl, decyl, undecyl, dodecyl, cyclo-pentyl, cyclohexyl, methylcyclohexyl, phenyl, benzyl, methylphenyl, methylbenzyl, methoxy-phenyl, dimethoxyphenyl and methoxybenzyl.

An arylene group T preferably has from 6 to 14 carbon atoms. Examples of arylene are phenylene, naphthylene, anthracylene and phenanthrylene. Preference is given to phenylene and naphthylene.

The secondary phosphine groups $X_1$ and $X_2$ can contain two identical hydrocarbon radicals or two different hydrocarbon radicals. The secondary phosphine groups $X_1$ and $X_2$ preferably contain have two identical hydrocarbon radicals. Furthermore, the secondary phosphine groups $X_1$ and $X_2$ can be identical or different.

The hydrocarbon radicals can be unsubstituted or substituted and/or contain heteroatoms selected from the group consisting of O, S and N($C_1$-$C_4$-alkyl). They can have from 1 to 22 carbon atoms, preferably from 1 to 12 carbon atoms and particularly preferably from 1 to 8 carbon atoms. A preferred secondary phosphine is that in which the phosphine group contains two identical or different radicals selected from the group consisting of linear or branched, $C_1$-$C_{12}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl, naphthyl, furyl or benzyl; and phenyl or benzyl substituted by halogen (for example F, Cl and Br), $C_1$-$C_6$-alkyl, $C_1$-$C_6$-haloalkyl (for example trifluoromethyl), $C_1$-$C_6$-alkoxy, $C_1$-$C_6$-haloalkoxy (for example trifluoromethoxy), $(C_6H_5)_3Si$, $(C_1$-$C_{12}$-alkyl$)_3$Si, secondary amino or —$CO_2$—$C_1$-$C_6$-alkyl (for example —$CO_2CH_3$).

Examples of alkyl substituents on P, which preferably have from 1 to 6 carbon atoms, are methyl, ethyl, n-propyl, i-propyl, n-butyl, i-butyl, t-butyl and the isomers of pentyl and hexyl. Examples of cycloalkyl substituents on P, which may be unsubstituted or alkyl-substituted, are cyclopentyl, cyclohexyl, methylcyclohexyl and ethylcyclohexyl and dimethylcyclohexyl. Examples of alkyl-, alkoxy-, haloalkyl- and haloalkoxy-substituted phenyl and benzyl substituents on P are methylphenyl, dimethylphenyl, trimethylphenyl, ethylphenyl, methyl-benzyl, methoxyphenyl, dimethoxyphenyl, trifluoromethylphenyl, bistrifluoromethylphenyl, tristrifluoromethylphenyl, trifluoromethoxyphenyl, bistrifluoromethoxyphenyl and 3,5-dimethyl-4-methoxyphenyl.

Preferred secondary phosphine groups are ones containing identical radicals selected from the group consisting of $C_1$-$C_6$-alkyl, cyclopentyl or cyclohexyl which may be unsubstituted or substituted by from 1 to 3 $C_1$-$C_4$-alkyl or $C_1$-$C_4$-alkoxy groups, benzyl and in particular phenyl which may be unsubstituted or substituted by from 1 to 3 $C_1$-$C_4$-alkyl, $C_1$-$C_4$-alkoxy, F, Cl, $C_1$-$C_4$-fluoroalkyl or $C_1$-$C_4$-fluoroalkoxy groups.

The secondary phosphino group preferably corresponds to the formula —$PR_3R_4$, where $R_3$ and $R_4$ are each, independently of one another, a hydrocarbon radical which has from 1 to 18 carbon atoms and may be unsubstituted or substituted by halogen, $C_1$-$C_6$-alkyl, $C_1$-$C_6$-haloalkyl, $C_1$-$C_6$-alkoxy, $C_1$-$C_6$-haloalkoxy, ($C_1$-$C_4$-alkyl)$_2$-amino, ($C_6H_5$)$_3$Si, ($C_1$-$C_{12}$-alkyl)$_3$Si or —$CO_2$—$C_1$-$C_6$-alkyl and/or contains heteroatoms O.

$R_3$ and $R_4$ are preferably identical radicals selected from the group consisting of linear or branched $C_1$-$C_6$-alkyl, unsubstituted cyclopentyl or cyclohexyl or cyclopentyl or cyclohexyl substituted by from one to three $C_1$-$C_4$-alkyl or $C_1$-$C_4$-alkoxy groups, furyl, unsubstituted benzyl or benzyl substituted by from one to three $C_1$-$C_4$-alkyl or $C_1$-$C_4$-alkoxy groups and, in particular, unsubstituted phenyl or phenyl substituted by from one to three $C_1$-$C_4$-alkyl, $C_1$-$C_4$-alkoxy, —$NH_2$, OH, F, Cl, $C_1$-$C_4$-fluoroalkyl or $C_1$-$C_4$-fluoroalkoxy groups.

$R_3$ and $R_4$ are particularly preferably identical radicals selected from the group consisting of $C_1$-$C_6$-alkyl, cyclopentyl, cyclohexyl, furyl, and unsubstituted phenyl or phenyl substituted by from one to three $C_1$-$C_4$-alkyl, $C_1$-$C_4$-alkoxy and/or $C_1$-$C_4$-fluoroalkyl groups.

The secondary phosphine groups $X_1$ and $X_2$ can be cyclic secondary phosphino groups, for example groups of the formulae

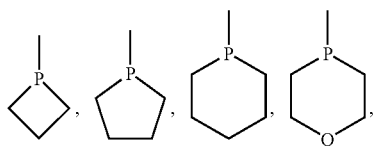

which may be unsubstituted or monosubstituted or polysubstituted by —OH, $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkylphenyl or $C_1$-$C_4$-alkoxyphenyl, benzyl, $C_1$-$C_4$-alkylbenzyl or $C_1$-$C_4$-alkoxybenzyl, benzyloxy, $C_1$-$C_4$-alkylbenzyloxy or $C_1$-$C_4$-alkoxybenzyloxy or $C_1$-$C_4$-alkylidenedioxyl.

The substituents can be bound in one or both of the a positions relative to the P atom in order to introduce chiral carbon atoms. Substituents in one or both a positions are preferably $C_1$-$C_4$-alkyl or benzyl, for example methyl, ethyl, n- or i-propyl, benzyl or —$CH_2O$—$C_1$-$C_4$-alkyl or —$CH_2$—O—$C_6$-$C_{10}$-aryl.

Substituents in the β,γ positions can be, for example, $C_1$-$C_4$-alkyl, $C_1$-$C_4$-alkoxy, benzyloxy or —O—$CH_2$—O—, —O—CH($C_1$-$C_4$-alkyl)-O— and —O—C($C_1$-$C_4$-alkyl)$_2$-O—. Some examples are methyl, ethyl, methoxy, ethoxy, —O—CH(methyl)-O— and —O—C(methyl)$_2$-O—.

Depending on the type of substituent(s) and the number of substituents, the cyclic phosphine radicals can be C-chiral, P-chiral or C- and P-chiral.

In the radicals of the above formulae, an aliphatic 5- or 6-membered ring or benzene can be fused onto two adjacent carbon atoms.

The cyclic secondary phosphino can correspond, for example, to the formulae (only one of the possible diastereomers is indicated),

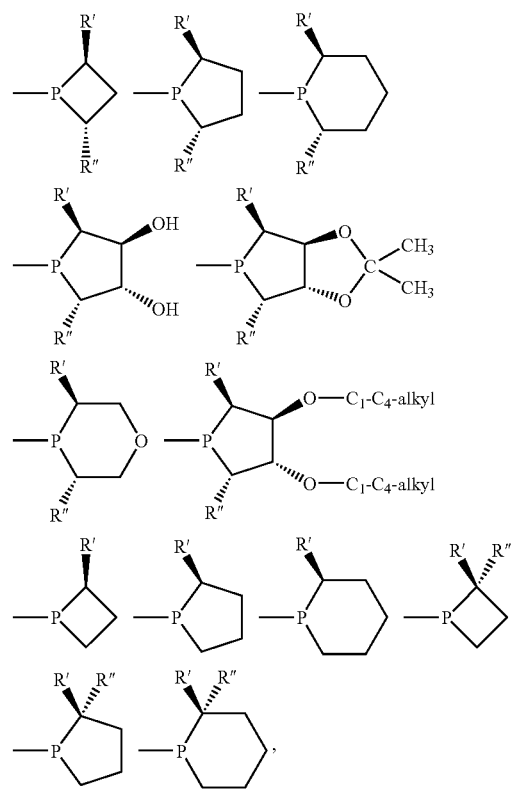

where the radicals R' and R" are each $C_1$-$C_4$-alkyl, for example methyl, ethyl, n- or i-propyl, benzyl, or —$CH_2$—O—$C_1$-$C_4$-alkyl or —$CH_2$—O—$C_6$-$C_{10}$-aryl, and R' and R" are identical or different.

In a preferred embodiment, the compounds of the invention correspond to diastereomers of the formulae Ic, Id, Ie and If,

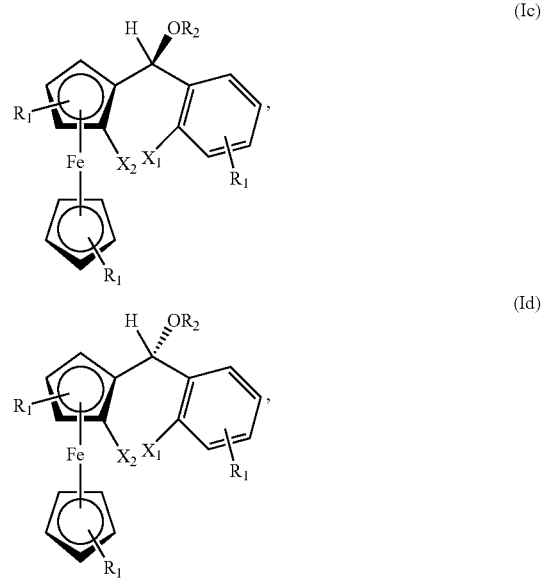

-continued

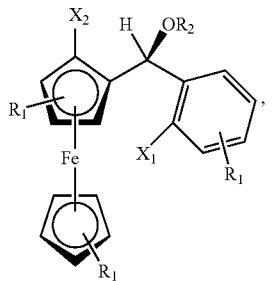
(Ie)

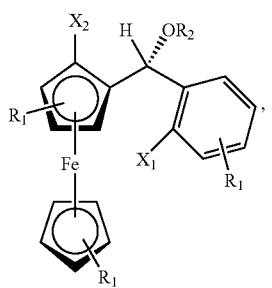
(If)

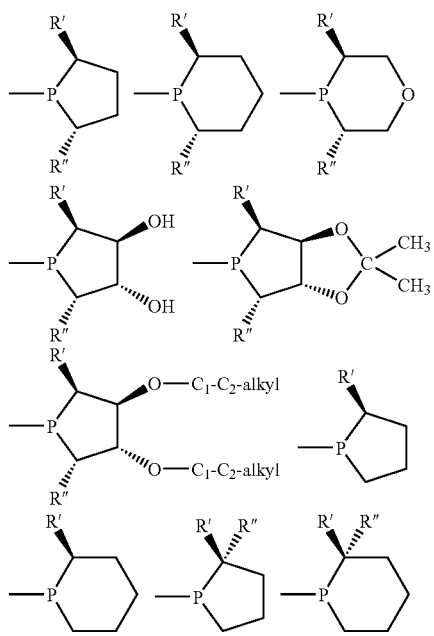

where
R$_1$ is hydrogen and X$_1$ and X$_2$ have the meanings indicated above, including the preferences.

In the compounds of the formulae Ic, Id, Ie and If, X$_1$ and X$_2$ are preferably identical or different acyclic secondary phosphine selected from the group consisting of —P(C$_1$-C$_6$-alkyl)$_2$, —P(C$_5$-C$_8$-cycloalkyl)$_2$, —P(C$_7$-C$_8$-bicycloalkyl)$_2$, —P(C$_5$-C$_8$-cycloalkyl)$_2$-P(o-furyl)$_2$, —P(C$_6$H$_5$)$_2$, —P[2-(C$_1$-C$_6$-alkyl)C$_6$H$_4$]$_2$, —P[3-(C$_1$-C$_6$-alkyl)C$_6$H$_4$]$_2$, —P[4-(C$_1$-C$_6$-alkyl)C$_6$H$_4$]$_2$, —P[2-(C$_1$-C$_6$-alkoxy)C$_6$H$_4$]$_2$, —P[3-(C$_1$-C$_6$-alkoxy)C$_6$H$_4$]$_2$, —P[4-(C$_1$-C$_6$-alkoxy)C$_6$H$_4$]$_2$, —P[2-(trifluoromethyl)C$_6$H$_4$]$_2$, —P[3-(trifluoromethyl)C$_6$H$_4$]$_2$, —P[4-(trifluoromethyl)C$_6$H$_4$]$_2$, —P[3,5-bis(trifluoromethyl)C$_6$H$_3$]$_2$, —P[3,5-bis(C$_1$-C$_6$-alkyl)$_2$C$_6$H$_3$]$_2$, —P[3,5-bis(C$_1$-C$_6$-alkoxy)$_2$C$_6$H$_3$]$_2$ and —P[3,5-bis(C$_1$-C$_6$-alkyl)$_2$-4-(C$_1$-C$_6$-alkoxy)C$_6$H$_2$]$_2$, or cyclic phosphine selected from the group consisting of

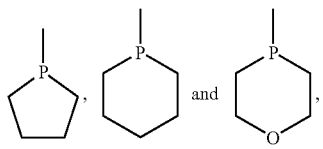

which may be unsubstituted or monosubstituted or polysubstituted by C$_1$-C$_4$-alkyl, C$_1$-C$_4$-alkoxy, C$_1$-C$_4$-alkoxy-C$_1$-C$_2$-alkyl, phenyl, benzyl, benzyloxy or C$_1$-C$_4$-alkylidenedioxyl.

Some specific examples are —P(CH$_3$)$_2$, —P(i-C$_3$H$_7$)$_2$, —P(n-C$_4$H$_9$)$_2$, —P(i-C$_4$H$_9$)$_2$, —P(C$_6$H$_{11}$)$_2$, —P(norbornyl)$_2$, —P(o-furyl)$_2$, —P(C$_6$H$_5$)$_2$, P[2-(methyl)C$_6$H$_4$]$_2$, P[3-(methyl)C$_6$H$_4$]$_2$; —P[4-(meth-yl)C$_6$H$_4$]$_2$, —P[2-(methoxy)C$_6$H$_4$]$_2$, —P[3-(methoxy)C$_6$H$_4$]$_2$, —P[4-(methoxy)C$_6$H$_4$]$_2$, —P[3-(tri-fluoromethyl)C$_6$H$_4$]$_2$, —P[4-(trifluoromethyl)C$_6$H$_4$]$_2$, —P[3,5-bis(trifluoromethyl)C$_6$H$_3$]$_2$, —P[3,5-bis-(methyl)$_2$C$_6$H$_3$]$_2$, —P[3,5-bis(methoxy)$_2$C$_6$H$_3$]$_2$ and —P[3,5-bis(methyl)$_2$-4-(methoxy)C$_6$H$_2$]$_2$, and groups of the formulae where
R' is methyl, ethyl, methoxy, ethoxy, phenoxy, benzyloxy, methoxymethyl, ethoxymethyl or benzyloxymethyl and R" has the same meanings as R'.

The ferrocene diphosphines of the invention can be prepared by a novel process in which a regioselective and stereoselective ortho-metallation of ferrocenylmonophosphines having PN-bonded, chiral radicals represents the key step in the reaction sequence. The process is modular for the creation of different substituents on the two P atoms and gives high yields. In addition, pure diastereomers can be prepared directly or pairs of easily separated diastereomers can be prepared, in each case in a simple manner and in high yields. The process is particularly useful for the preparation of the diphosphines of the invention on an industrial scale.

The preparative process comprises the following steps. In a first process step, an essentially optically pure halodi(secondary-amino)phosphine containing chiral amino groups is provided. Such phosphines can be prepared in a simple manner by reacting PCl$_3$ or PBr$_3$ with about 2 equivalents of an optically pure, chiral, secondary amine in the presence of a halogen scavenger such as a tertiary amine (triethylamine). Cyclic secondary amines having a chiral C atom in the a position relative to the N atom are advantageously used. An example which may be mentioned is di[(S)- or (R)-α-methoxymethylpyrrolodino]chloro-phosphine of the formulae

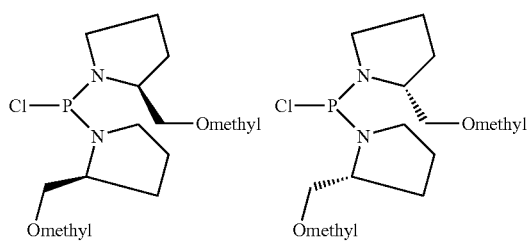

The halodi(secondary-amino)phosphines are reacted with unsubstituted or $R_1$-substituted and metallated ferrocene, for example Li-ferrocene, to form compounds of the formula A

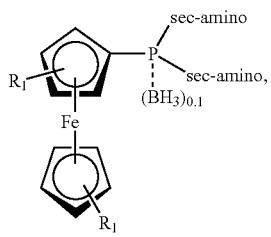
(A)

with borane being able to be introduced as protective group (for example by reaction with borane-dimethyl sulphide) prior to isolation. This intermediate is reacted in a process step a) with at least equivalent amounts of an alkyllithium, a magnesium Grignard compound or an aliphatic lithium secondary-amide or $X_3$Mg-secondary amide to form compounds of the formula B1 or B2,

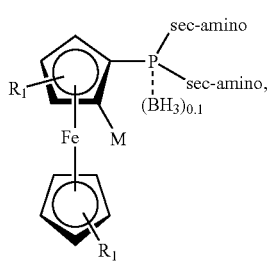
(B1)

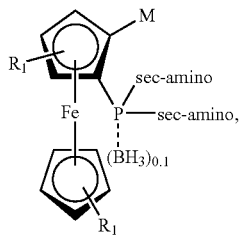
(B2)

where

M is —Li or —$MgX_3$ and $X_3$ is Cl, Br or I. The compounds can be used in the next step without intermediate isolation.

In a process step b), the compounds of the formula B1 or B2 are then reacted with at least two equivalents of an aldehyde of the formula $(R_1)_vT(o\text{-}X_4)\text{—}C(\!\!=\!\!O)H$, hereinafter more preferably a preferred phenylaldehyde of the formula C,

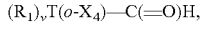
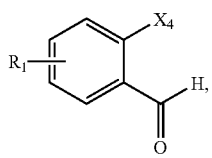
(C)

where $R_1$ and v have the meanings given above and $X_4$ is Cl, Br or I or secondary-phosphino $X_1$, to form compounds of the formula D1 or D2

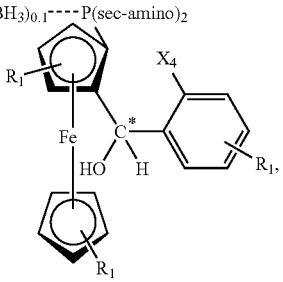
(D1)

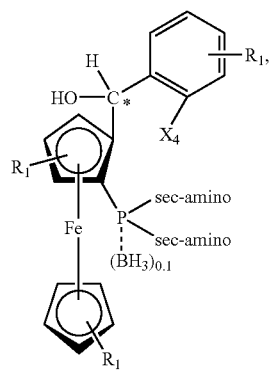
(D2)

The compounds of the formulae D1 and D2 are mixtures of diastereomers in which one can be present in excess. In this step, pure diastereomers of the formulae D3 and D4 or D5 and D6 can easily be obtained by, for example, chromatographic methods (by means of separation on silica gels) or crystallization methods:

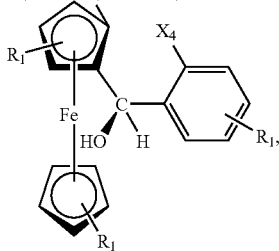
(D3)

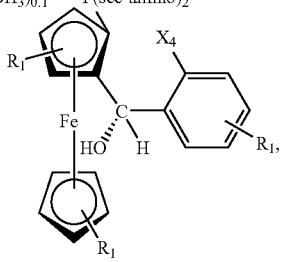
(D4)

-continued

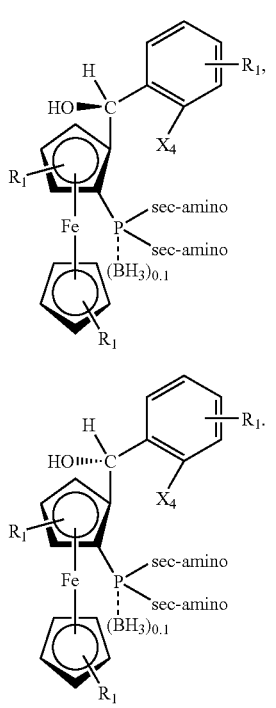
(D5)

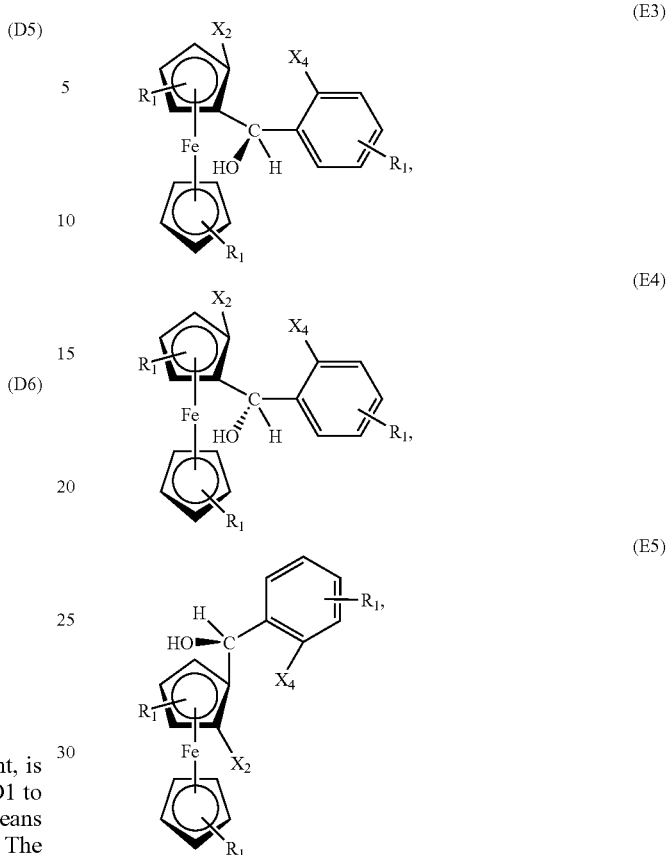
(E3)

(E4)

(E5)

(D6)

(E6)

In a next process step c), the borane group, if present, is removed from one of the compounds of the formulae D1 to D6, then the secondary amino radical is eliminated by means of HCl or HBr to form a —$PCl_2$ group or —$PBr_2$ group. The intermediate products can be isolated or directly reacted further to form secondary, acyclic or cyclic phosphine groups from the $PCl_2$ or $PBr_2$ groups.

For this purpose, the Cl or Br atoms are reacted with at least two equivalents of an organometallic compound or one equivalent of a bisorganometallic compound (Grignard reagents) and replaced by a hydrocarbon radical to form an acyclic or cyclic secondary phosphine of the formulae E1 to E6 in a known manner in a process step d):

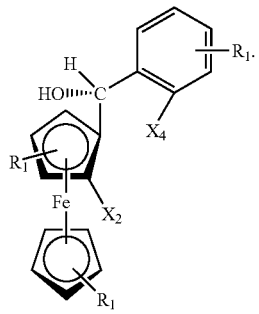
(E1)

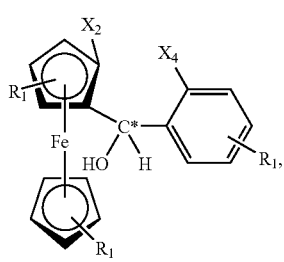
(E2)

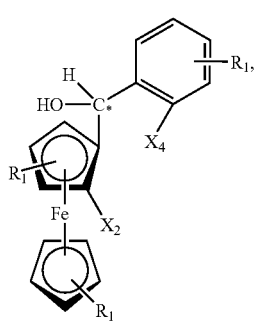

When $X_4$ is secondary phosphine $X_1$, this step leads directly to the compounds of the invention.

The $PCl_2$ or —$PBr_2$ groups can be hydrogenated in a simple manner to form primary phosphine groups. Primary phosphine groups can be converted into cyclic phosphine groups in a manner known per se by means of known alkylating agents such as cyclic sulphates, sulphonates or phosphonates or open-chain disulphonates.

When $X_4$ is Cl, Br or I, one of the compounds of the formulae E1 to E6 is reacted with at least 1 equivalent of a lithium alkyl and then with at least 1 equivalent of secondary-phosphine halide ($X_1$ halide, halide such as Cl or Br) in a further process step e) to form a compound according to the invention. As an alternative, compounds of the formulae E1 to E6 can also be reacted with previously formed lithium sec-ondary-phosphide $L_1$-$X_1$. Before these reactions, the OH group is made inert, for example by metallation with a metal hydride such as LiH, NaH or KH.

Lithium alkyl in the process step a) can be, for example, Li($C_1$-$C_4$-alkyl) or Li-phenyl, e.g. Li-methyl, Li-n-, Li-s- or Li-t-butyl.

Aliphatic lithium secondary-amide or $X_3$Mg secondary-amide in step a) can be derived from secondary amines having from 2 to 18 carbon atoms, preferably from 2 to 12 carbon atoms and particularly preferably from 2 to 10 carbon atoms. The aliphatic radicals bound to the N atom can be alkyl, cycloalkyl or cycloalkylalkyl, or N-heterocyclic rings having from 4 to 12 carbon atoms, preferably from 5 to 7 carbon atoms, can be present. Examples of radicals bound to the N atom are methyl, ethyl, n-propyl, n-butyl, pentyl, hexyl, cyclopentyl, cyclo-hexyl and cyclohexylmethyl. Examples of N-heterocyclic rings are pyrrolidine, piperidine, morpholine, N-methylpiperazine, 2,2,6,6-tetramethylpiperidine and aza-norbornane.

In a preferred embodiment, Li-alkyl or Li-phenyl is used in process step a).

The metallation of aromatics involves known reactions as are described, for example, by M. Schlosser (editor) in Organometallics in Synthesis, John Wiley & Sons (1994) or in Jonathan Clayden Organolithiums: Selectivity for Synthesis (Tetrahedron Organic Chemistry Series), Pergamon Press (2002).

For the purposes of the invention, "at least equivalent amounts" refers to the use of from 1 to 1.2 equivalents of an Li-alkyl or magnesium Grignard compound, or an aliphatic lithium secondary-amide or $X_3$Mg-secondary-amide per reacting =CH group in the cyclopentadienyl ring.

The reaction is advantageously carried out at low temperatures, for example at from 20 to −100° C., preferably from 10 to −50° C. The reaction time is from about 2 to 5 hours. The reaction is advantageously carried out under an inert protective gas, for example nitrogen or a noble gas such as argon.

The reaction is advantageously carried out in the presence of inert solvents. Such solvents can be used alone or as a combination of at least two solvents. Examples of solvents are aliphatic, cycloaliphatic and aromatic hydrocarbons and also open-chain or cyclic ethers. Specific examples are petroleum ether, pentane, hexane, heptane, cyclohexane, methylcyclohexane, benzene, toluene, xylene, diethyl ether, dibutyl ether, tert-butyl methyl ether, ethylene glycol dimethyl or diethyl ether, tetrahydrofuran and dioxane.

In the reaction in process step b), "at least equivalent amounts" refers, for the purposes of the invention, to the use of from 1 to 1.2 equivalents of aldehyde of the formula C per reacting =CM group in the ferrocene. However, it is also possible to use a substantial excess of up to 2.5 equivalents.

The reaction is advantageously carried out at low temperatures, for example at from 20 to −100° C., preferably from 0 to 80° C. The reaction is advantageously carried out under an inert protective gas, for example a noble gas such as argon or else nitrogen. After addition of the compound C, the mixture is advantageously allowed to warm to room temperature or is warmed to elevated temperatures, for example up to 100° C. and preferably up to 50° C., and is stirred for some time under these conditions to complete the reaction.

The reaction is advantageously carried out in the presence of inert solvents. Such solvents can be used alone or as a combination of at least two solvents. Examples of solvents are aliphatic, cycloaliphatic and aromatic hydrocarbons and also open-chain or cyclic ethers. Specific examples are petroleum ether, pentane, hexane, heptane, cyclohexane, methylcyclohexane, benzene, toluene, xylene, diethyl ether, dibutyl ether, tert butyl methyl ether, ethylene glycol dimethyl or diethyl ether, tetrahydrofuran and dioxane.

Isolation of the compounds of the formulae D1 to D6 can be carried out by methods known per se, for example extraction, filtration and distillation. After isolation, the compounds can be purified, for example by distillation, recrystallization or by chromatographic methods.

It has surprisingly been found that the reaction of the metallated and in particular lithiated ferrocenes with the prochiral compound C leads to a very high diastereoselectivity in respect of the planar chirality (ferrocene skeleton) and in addition to a significant diastereoselectivity in respect of the chirality on the prochiral carbon atom. On introduction of compound C, essentially only one pair of diastereomers in respect of planar chirality is formed, while four diastereomers are possible, and it is often also observed that one diastereomer of the diastereomeric pair is predominantly formed. Pure diastereomers can, if necessary at all, then easily be obtained in this step by separation by means of recrystallization or, in particular, chromatographic methods.

The reactions of the process steps c) to e) are known per se and are described in the literature.

The elimination of the borane group can, for example, be effected by addition of reagents such as secondary amines having $C_1$-$C_4$-alkyl groups, morpholine, 1,8-diazabicyclo[5.4.0]-undec-7-ene (DBU), 1,4-diazabicyclo[2.2.2]octane, sufficiently long stirring at temperatures of from 20 to 100° C. and removal of the volatile constituents, advantageously under reduced pressure. Methods for the removal of borane are described, for example, by M. Ohff et al. in Synthesis (1998), page 1391. The removal of the borane group only in the last reaction step offers the advantage that reaction-sensitive groups remain protected.

The formation of —$PCl_2$ or —$PBr_2$ groups is likewise known and is described, for example, by A. Longeau et al. in Tetrahedron: Asymmetry, 8 (1997), pages 987-990. Reagents used are advantageously organic solutions of HCl or HBr in, for example, ethers, which are added at low temperatures (for example from −20 to 30° C.) to dissolved compounds of the formula VII, IX or XI with or without a borane group.

The Grignard reagents used in process step d) can be Li—, ClMg—, BrMg— or IMg-hydro-carbons which are generally added in excess, for example up to 5 equivalents per halogen atom. The reaction is carried out in solution, with solvents as mentioned above for the metallation being able to be used. The reaction can be carried out at temperatures of from −80 to 80° C.

The reactions for introducing an acyclic or cyclic secondary-phosphine group in process step e) are known per se and are illustrated in the examples.

In the compounds of the formulae E1 to E6, the OH group can, if desired, be converted into the group —$OR_2$, for example by means of silyl halides, substituted acid derivatives such as esters and halides, carbonates or isocyanates. Large numbers of reagents for introducing these groups are known. As an alternative, the compounds of the formulae Ia to If in which $R_2$ is H can be converted in the same way into new ligands in which $R_2$ has the meanings given for the formula I with the exception of hydrogen. Known ligands in which $R_2$ is alkyl or unsubstituted acyl can be prepared in an analogous way. Compounds according to the invention can also be bound covalently to a polymer in a known manner via the OH group ($R_2$ is H), either directly or via a bridging group, to immobilize and produce catalysts which can be separated off.

The invention also provides the intermediates of the formulae F to F',

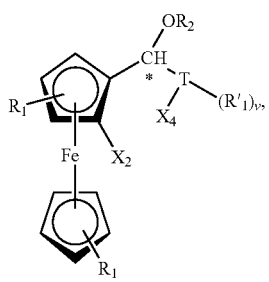

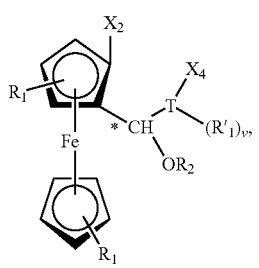

and preferably the formulae F1 to F6

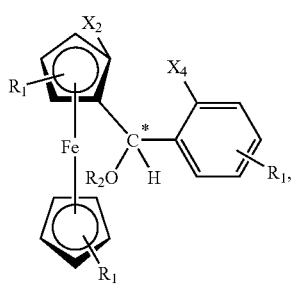 (F1)

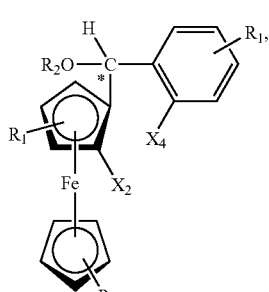 (F2)

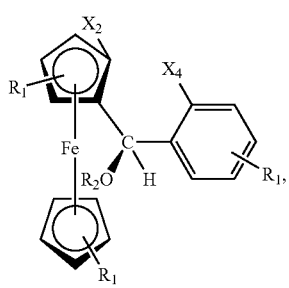 (F3)

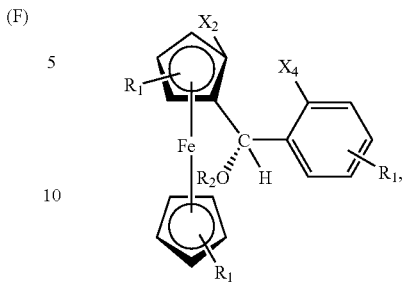 (F)

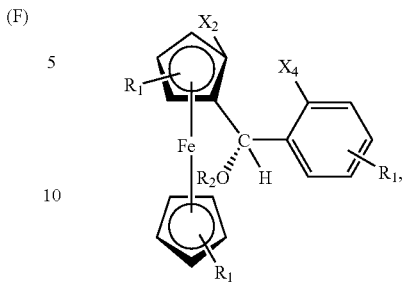 (F')

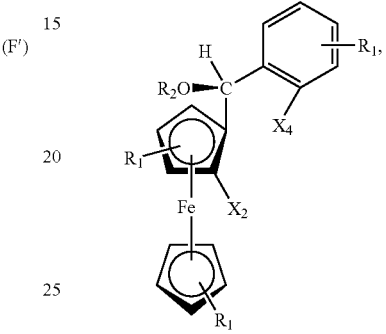 (F4)

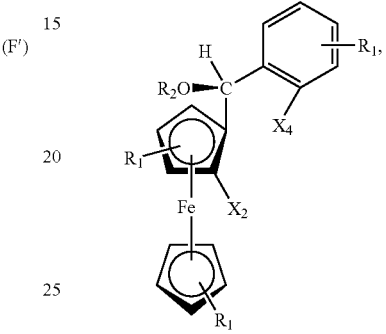 (F5)

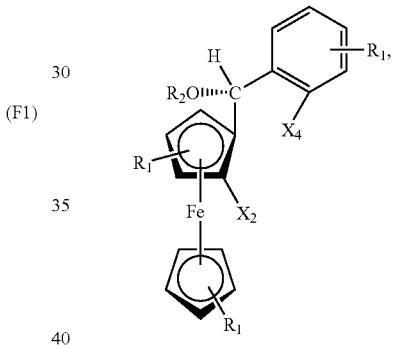 (F6)

where

T, $R_1$, $R'_1$ and v have the meanings given above, $R_2$ is H and $X_4$ is Cl, Br or I. In the case of v, $R_1$, $R'_1$ and $X_4$, the above-mentioned preferences apply.

The novel compounds of the formulae I and I', preferably Ia to If, are ligands for metal complexes selected from the group of TM8 metals, in particular from the group consisting of Ru, Rh and Ir, which are excellent catalysts or catalyst precursors for asymmetric syntheses, for example the asymmetric hydrogenation of prochiral, unsaturated, organic compounds. If prochiral unsaturated organic compounds are used, a very high excess of optical isomers can be induced in the synthesis of these organic compounds and a high chemical conversion can be achieved in short reaction times. The achievable enantioselectivities and catalyst activities are excellent.

The invention further provides metal complexes of metals selected from the group of TM8 metals with one of the compounds of the formula I or I' and preferably Ia to If as ligands.

Possible metals are, for example, Cu, Ag, Au, Ni, Co, Rh, Pd, Ir, Ru and Pt. Preferred metals are rhodium and iridium and also ruthenium, platinum and palladium.

Particularly preferred metals are ruthenium, rhodium and iridium.

The metal complexes can, depending on the oxidation number and coordination number of the metal atom, contain further ligands and/or anions. They can also be cationic metal complexes. Such analogous metal complexes and their preparation are widely described in the literature.

The metal complexes can, for example, correspond to the general formulae II and III,

$$A_1MeL_n \quad (II)$$

$$(A_1MeL_n)^{(z+)}(E^-)_z \quad (III),$$

where $A_1$ is one of the compounds of the formula I or I', preferably Ia to If, L represents identical or different monodentate, anionic or nonionic ligands or L represents identical or different bidentate, anionic or nonionic ligands;

n is 2, 3 or 4 when L is a monodentate ligand, or n is 1 or 2 when L is a bidentate ligand;

z is 1, 2 or 3;

Me is a metal selected from the group consisting of Rh, Ir and Ru; with the metal having the oxidation state 0, 1, 2, 3 or 4;

$E^-$ is the anion of an oxo acid or a complex acid; and the anionic ligands balance the charge of the oxidation state 1, 2, 3 or 4 of the metal.

The preferences and embodiments described above apply to the compounds of the formulae I and I' and Ia to If.

Monodentate nonionic ligands can, for example, be selected from the group consisting of olefins (for example ethylene, propylene), solvating solvents, nitriles, linear or cyclic ethers, unalkylated or N-alkylated amides and lactams, amines, phosphines, alcohols, carboxylic esters, sulphonic esters), nitrogen monoxide and carbon monoxide.

Suitable polydentate anionic ligands are, for example, allyls (allyl, 2-methallyl), or deprotonated 1,3-diketo compounds such as acetylacetonate.

Monodentate anionic ligands can, for example, be selected from the group, consisting of halide (F, Cl, Br, I), pseudohalide (cyanide, cyanate, isocyanate) and anions of carboxylic acids, sulphonic acids and phosphonic acids (carbonate, formate, acetate, propionate, methylsulphonate, trifluoromethylsulphonate, phenylsulphonate, tosylate).

Bidentate nonionic ligands can, for example, be selected from the group consisting of linear and cyclic diolefins (for example hexadiene, cyclooctadiene, norbornadiene), dinitriles (malononitrile), unalkylated or N-alkylated carboxylic diamides, diamines, diphosphines, diols, dicarboxylic diesters and disulphonic diesters.

Bidentate anionic ligands can, for example, be selected from the group consisting of the anions of dicarboxylic acids, disulphonic acids and diphosphonic acids (for example of oxalic acid, malonic acid, succinic acid, maleic acid, methylenedisulphonic acid and methylenediphosphonic acid).

Preferred metal complexes also include ones in which E is $-Cl^-$, $-Br^-$, $-I^-$, $ClO_4^-$, $CF_3SO_3^-$, $CH_3SO_3^-$, $HSO_4^-$, $(CF_3SO_2)_2N^-$, $(CF_3SO_2)_3C^-$, tetraarylborates such as B(phenyl)$_4^-$, B[bis(3,5-trifluoromethyl)phenyl]$_4^-$, B[bis(3,5-dimethyl)phenyl]$_4^-$, B($C_6F_5$)$_4^-$ and B(4-methylphenyl)$_4^-$, $BF_4^-$, $PF_6^-$, $SbCl_6^-$, $AsF_6^-$ or $SbF_6^-$.

Very particularly preferred metal complexes which are particularly suitable for hydrogenations correspond to the formulae IV and V,

$$[A_1Me_2YZ] \quad (IV),$$

$$[A_1Me_2Y]^+E_1^- \quad (V),$$

where $A_1$ is one of the compounds of the formula I or I', preferably Ia or Ib;

$Me_2$ is rhodium or iridium;

Y represents two olefins or a diene;

Z is Cl, Br or I; and $E_1^-$ is the anion of an oxo acid or complex acid.

The above-described embodiments and preferences apply to the compounds of the formulae I and I' and Ia to If.

When Y represents two olefins, the olefins can be $C_2$-$C_{12}$-, preferably $C_2$-$C_6$- and particularly preferably $C_2$-$C_4$-Olefins. Examples are propene, 1-butene and in particular ethylene. The diene can have from 5 to 12 carbon atoms, preferably from 5 to 8 carbon atoms, and can be an open-chain, cyclic or polycyclic diene. The two olefin groups of the diene are preferably connected by one or two $CH_2$ groups. Examples are 1,4-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y preferably represents two ethylene molecules or 1,5-hexadiene, 1,5-cyclooctadiene or norbornadiene.

In the formula XVI, Z is preferably Cl or Br. Examples of $E_1$ are $BF_4^-$, $ClO_4^-$, $CF_3SO_3^-$, $CH_3SO_3^-$, $HSO_4^-$, B(phenyl)$_4^-$, B[bis(3,5-trifluoromethyl)phenyl]$_4^-$, $PF_6^-$, $SbCl_6^-$, $AsF_6^-$ and $SbF_6^-$.

The metal complexes of the invention are prepared by methods known from the literature (cf. U.S. Pat. No. 5,371,256, U.S. Pat. No. 5,446,844, U.S. Pat. No. 5,583,241 and E. Jacobsen, A. Pfaltz, H. Yamamoto (Eds.), Comprehensive Asymmetric Catalysis I to III, Springer Verlag, Berlin, 1999, and references cited therein).

The metal complexes of the invention are homogeneous catalysts or catalyst precursors which can be activated under the reaction conditions, and can be used for asymmetric addition reactions of prochiral, unsaturated, organic compounds.

The metal complexes can, for example, be used for the asymmetric hydrogenation (addition of hydrogen) of prochiral compounds having carbon-carbon or carbon-heteroatom double bonds. Such hydrogenations using soluble homogeneous metal complexes are described, for example, in Pure and Appl. Chem., Vol. 68, No. 1, pp. 131-138 (1996). Preferred unsaturated compounds to be hydrogenated contain the groups C=C, C=N and/or C=O. According to the invention, metal complexes of ruthenium, rhodium and iridium are preferably used for the hydrogenation.

The invention further provides for the use of the metal complexes of the invention as homogeneous catalysts for preparing chiral organic compounds by asymmetric addition of hydrogen onto a carbon-carbon or carbon-heteroatom double bond in prochiral organic compounds.

The invention also provides a process for preparing chiral organic compounds by asymmetric addition of hydrogen onto a carbon-carbon or carbon-heteroatom double bond in prochiral organic compounds in the presence of a catalyst, which is characterized in that the addition reaction is carried out in the presence of catalytic amounts of at least one metal complex according to the invention.

Preferred prochiral, unsaturated compounds to be hydrogenated can contain one or more, identical or different groups C=C, C=N and/or C=O, in open-chain or cyclic organic compounds, with the groups C=C, C=N and/or C=O being able to be part of a ring system or being exocyclic groups. The prochiral unsaturated compounds can be alkenes, cycloalkenes, heterocycloalkenes or open-chain or cyclic ketones, α,β-diketones, α- or β-ketocarboxylic acids or their α,β-ketoacetals or -ketals, esters and amides, ketimines and ketohydrazones.

Some examples of unsaturated organic compounds are acetophenone, 4-methoxy-acetophenone, 4-trifluoromethylacetophenone, 4-nitroacetophenone, 2-chloroacetophenone, corresponding unsubstituted or N-substtuted acetophenonebenzylimines, unsubstituted or substituted benzocyclohexanone or benzocyclopentanone and corresponding imines, imines from the group consisting of unsubstituted or substituted tetrahydroquinoline, tetrahydro-pyridine and dihydropyrrole, and unsaturated carboxylic acids, esters, amides and salts such as α- and, if appropriate, β-substituted acrylic acids or crotonic acids. Preferred carboxylic acids are those of the formula $R_{01}$—CH=C($R_{02}$)—C(O)OH and also their salts, esters and amides, where $R_{01}$ is $C_1$-$C_6$-alkyl, unsubstituted $C_3$-$C_8$-cycloalkyl or cycloalkyl substituted by from 1 to 4 $C_1$-$C_6$-alkyl, $C_1$-$C_6$-alkoxy, $C_1$-$C_6$-alkoxy-$C_1$-$C_4$-alkoxy groups, or unsubstituted $C_6$-$C_{10}$-aryl or $C_6$-$C_{10}$-aryl substituted by from 1 to 4 $C_1$-$C_6$-alkyl, $C_1$-$C_6$-alkoxy, $C_1$-$C_6$-alkoxy-$C_1$-$C_4$-alkoxy groups, preferably phenyl, and $R_{02}$ is linear or branched $C_1$-$C_6$-alkyl (for example isopropyl), or cyclopentyl, cyclohexyl or phenyl which may each be unsubstituted or substituted as defined above or protected amino (for example acetylamino).

The process of the invention can be carried out at low or elevated temperatures, for example temperatures of from −20 to 150° C., preferably from −10 to 100° C., and particularly preferably from 10 to 80° C. The optical yields are generally better at lower temperature than at higher temperatures.

The process of the invention can be carried out at atmospheric pressure or superatmospheric pressure. The pressure can be, for example, from $10^5$ to $2 \times 10^7$ Pa (pascal). Hydrogenations can be carried out at atmospheric pressure or at superatmospheric pressure.

Catalysts are preferably used in amounts of from 0.0001 to 10 mol %, particularly preferably from 0.001 to 10 mol % and very particularly preferably from 0.01 to 5 mol %, based on the compound to be hydrogenated.

The preparation of the ligands and catalysts and also the hydrogenation can be carried out in the absence of solvents or in the presence of an inert solvent, with one solvent or mixtures of solvents being able to be used. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogenated hydrocarbons (methylene chloride, chloroform, dichloroethane and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactone), N-substituted lactams (N-methylpyrrolidone), carboxamides (dimethylamide, dimethylformamide), acyclic ureas (dimethylimidazoline) and sulphoxides and sulphones (dimethyl sulphoxide, dimethyl sulphone, tetramethylene sulphoxide, tetramethylene sulphone) and alcohols (methanol, ethanol, propanol, butanol, ethylene glycol monomethyl ether, ethylene glycol monoethyl ether, diethylene glycol monomethyl ether) and water. The solvents can be used alone or as a mixture of at least two solvents.

The reaction can be carried out in the presence of cocatalysts, for example quaternary ammonium halides. (tetrabutylammonium iodide), and/or in the presence of protic acids, for example mineral acids (cf., for example, U.S. Pat. No. 5,371,256, U.S. Pat. No. 5,446,844 and U.S. Pat. No. 5,583,241 and EP-A-0 691 949). The presence of fluorinated alcohols such as 1,1,1-trifluoroethanol can likewise promote the catalytic reaction.

The metal complexes used as catalysts can be added as separately prepared, isolated compounds or can be formed in situ prior to the reaction and then be mixed with the substrate to be hydrogenated. It can be advantageous to add additional ligands in the reaction using isolated metal complexes or to use an excess of the ligands in the in-situ preparation. The excess can be, for example, from 1 to 6 mol, preferably from 1 to 2 mol, based on the metal compound used for the preparation.

The process of the invention is generally carried out by placing the catalyst in a reaction vessel and then adding the substrate, if appropriate reaction auxiliaries and the compound to be added on, and then starting the reaction. Gaseous compounds to be added on, for example hydrogen or ammonia, are preferably injected under pressure. The process can be carried out continuously or batchwise in various types of reactor.

The chiral organic compounds which can be prepared according to the invention are active substances or intermediates for the preparation of such substances, for example in the field of preparation of aromas and fragrances, pharmaceuticals and agrochemicals.

The following examples illustrate the invention.

A) Preparation of Intermediates

EXAMPLE A1

Preparation of

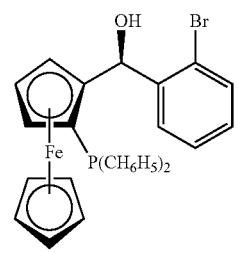

(1)

a) Preparation of

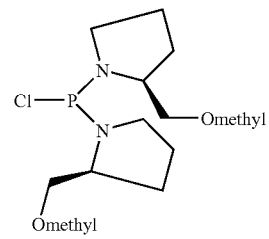

In a 500 ml round-bottomed flask provided with an argon inlet, $PCl_3$ (7.38 g, 53.75 mmol) is dissolved in dry tetrahydrofuran (THF, 150 ml) under argon and the solution is cooled to 0° C. in an ice bath. Triethylamine (11.97 g, 118.25 mmol, 2.20 equivalents) is added dropwise and (S)-methoxymethylpyrrolidine (12.69 g, 110.19 mmol, 2.05 equivalents) is subsequently slowly added dropwise. During the addition, the formation of a white precipitate is observed. The ice bath is removed and the suspension obtained is stirred overnight (14 h) at room temperature (RT). The white precipitate formed is filtered under argon by means of an invertible frit filter and washed with dry THF (2×25 ml). A $^{31}$P-NMR spectrum ($C_6D6$) of the yellowish filtrate obtained is recorded. The solution obtained in this way is reacted without further purification. $^{31}$P-NMR ($C_6D_6$, 121 MHz): 154.3 (s).

b) Preparation of

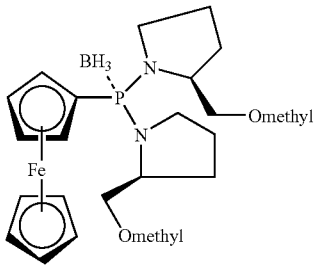

In a 1 l round-bottomed flask provided with an argon inlet, ferrocene (10.00 g, 53.75 mmol) and potassium t-butoxide (754 mg, 6.72 mmol, 0.125 equivalents) are dissolved in dry THF (100 ml) under argon. The solution is cooled to −78° C., and t-butyllithium (1.5 M in hexane; 71.67 ml, 107.50 mmol, 2.00 equivalents) is then added dropwise over a period of 45 minutes. The solution is stirred at −78° C. for 1.5 hours and admixed with heptane (75 ml). After the precipitate formed has settled, the supernatant solution is removed at −78° C. under argon by means of a transfer needle. The precipitate is washed with heptane (60 ml) at −78° C. and the washings are removed again by means of a transfer needle. This procedure is repeated three times. The precipitate obtained is dissolved in dry THF (50 ml) and a solution of the halophosphine prepared as described in a) (53.75 mmol, 1.00 equivalent) in THF (200 ml) is added at −78° C. over a period of 1.5 hours. The solution is stirred overnight (14 h) while warming to RT. Borane-dimethylsulphide complex (5.10 ml, 53.75 mmol, 1.00 equivalent) is subsequently added dropwise and the mixture is stirred overnight at RT. The reaction mixture is hydrolysed by means of saturated NH$_4$Cl solution (50 ml) and extracted with tert-butyl methyl ether (TBME, 3×100 ml). The combined organic phases are dried over Na$_2$SO$_4$ and the solvent is distilled off on a rotary evaporator. The crude product (24.18 g) is purified by column chromatography (200 g of silica gel, n-heptane/TBME 5:1). The title compound is obtained as an orange solid (17.23 g, 37.60 mmol, 70%).

$^1$H-NMR ($C_6D_6$): 4.22 (s, 5H Cp), 3.11 (s, 3H, OMe), 3.04 (s, 3H, OMe); $^{31}$P-NMR ($C_6D_6$, 121 MHz): 81.7-80.4 (m, br).

c) Preparation of (Me=methyl)

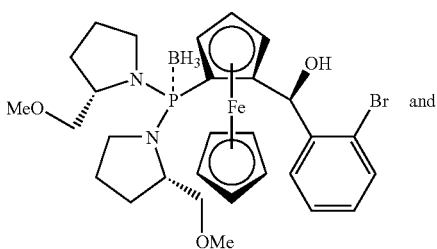

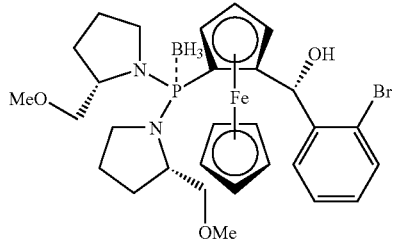

In a 100 ml round-bottomed flask provided with an argon inlet, the compound prepared as described in b) (1.00 g, 2.18 mmol) is dissolved in dry TBME (5.00 ml) and n-hexane (5.00 ml) and the solution obtained is cooled to −30° C. This results in precipitation of a yellow solid. s-Butyllithium (1.3 M in cyclohexane; 1.76 ml, 2.29 mmol, 1.05 equivalents) is added dropwise. This results in the yellow solid gradually going into solution, the solution becomes orange-red and an orange solid precipitates after about 30 minutes. After stirring at −30° C. for 2 hours, 2-bromobenzaldehyde (485 mg, 2.62 mmol, 2.2 equivalents) is added dropwise, the cooling bath is removed and the suspension is stirred overnight (14 h) while warming to RT. The reaction mixture is hydrolysed by means of saturated NH$_4$Cl solution, TBME (100 ml) is added, the organic phase is separated off and dried over Na$_2$SO$_4$. The solvent is distilled off on a rotary evaporator and the crude product is purified by column chromatography (200 g of silica gel, n-heptane/TBME 5:1). Compound (a) (849 mg, 1.32 mmol, 61%) and compound (b) (334 mg, 0.52 mmol, 24%) are obtained as orange-brown solids. In addition, the unreacted starting compound (150 mg, 0.33 mmol, 15%) is recovered in the form of a brown oil.

Compound (a) $^1$H-NMR ($C_6D_6$): 5.79 (d, 1H), 4.42 (s, 5H, Cp), 3.18 (s, 3H, OMe), 2.97 (s, 3H, OMe); $^{31}$P-NMR ($C_6D_6$, 121 MHz): 73.3 (m, br).

Compound (b) $^1$H-NMR ($C_6D_6$): 6.95 (d, 1H), 4.45 (s, 5H, Cp), 3.37 (s, 3H, OMe), 3.18 (s, 3H, OMe); $^{31}$P-NMR ($C_6D_6$, 121 MHz): 81.9 (m, br).

d) Preparation of the Title Compound (1)

In a 250 ml round-bottomed flask provided with an argon inlet, the ferrocenyl compound (a) (1.47 g, 2.29 mmol) is dissolved in a mixture of dry TBME (30 ml) and dry toluene (6 ml) and the solution is cooled to 0° C. HCl solution (2 M in diethyl ether; 4.57 ml, 9.14 mmol, 4.00 equivalents) is added dropwise, resulting in a colourless oil depositing on the wall of the vessel. After stirring overnight (14 h) at 0° C., the solution is evaporated to dryness in an oil pump vacuum. TBME (20 ml) is added and the white precipitate obtained is filtered off under argon by means of an immersion frit. The yellow filtrate is cooled, to −30° C. and phenyl MgBr solution (1 M in THF; 11.45 ml, 11.45 mmol, 5.00 equivalents) is added dropwise. The reaction mixture is stirred for 5 hours while warming to RT and hydrolysed by means of saturated NaHCO$_3$ solution (50 ml). The organic phase is separated off, the aqueous phase is extracted with TBME (100 ml), the combined organic phases are dried over Na$_2$SO$_4$ and the solvent is distilled off on a rotary evaporator. The crude product is dissolved in toluene (10 ml) under argon and 1,8-diazabicyclo[5.4.0]undec-7-ene (DBU) (767 mg, 5.04 mmol, 2.2 equivalents) is added. The reaction mixture is stirred at 80° C. for 2 hours and the solvent is distilled off on a rotary evaporator. The crude product obtained is purified by column chromatography (100 g of silica gel, n-heptane/TBME 5:1). The phosphane (1) is obtained as a yellow solid (953 mg, 75%).

$^1$H-NMR (C$_6$D$_6$), selected characteristic signals: 4.36 (s, br, 1H), 4.20 (s, 5H, Cp), 4.08 (s br, 1H), 3.85 (s, br, 1H); $^{31}$P-NMR (C$_6$D$_6$, 121 MHz): −21.8 (s).

EXAMPLE A2

Preparation of

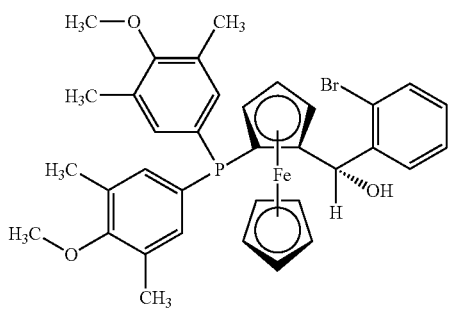

Using a method similar to that of Example Aid, compound (a) from Example A1c is reacted with bis(3,5-dimethyl-4-methoxyphenyl)magnesium bromide. The phosphane (2) is obtained as a yellow solid.

$^1$H-NMR (C$_6$D$_6$), selected characteristic signals: 4.08 (s, 5H, Cp), 3.24 (s, 6H, OCH$_3$), 3.20 (s, 6H, OCH$_3$), 2.05 (s, 6H, CH$_3$), 1.95 (s, 6H, CH$_3$); $^{31}$P-NMR (C$_6$D$_6$, 121 MHz): −23.3 (s).

B) Preparation of Diphosphines

EXAMPLE B1

Preparation of (S)-1-diphenylphosphino-2-[α-(S)-hydroxy(o-diphenylphos-phinophenyl)methyl]ferrocene of the formula (A)

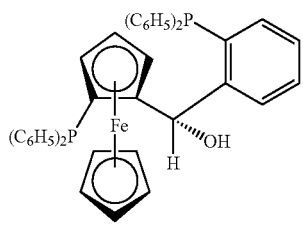

In a 100 ml round-bottomed flask provided with an argon inlet, potassium hydride (47 mg, 1.17 mmol, 1.30 equivalents) is suspended in dry THF (1.00 ml) under argon and the mixture is cooled to 0° C. Compound (1) (500 mg, 0.90 mmol) dissolved in dry THF (4.00 ml) is added dropwise and the solution obtained is stirred at RT for 1 hour. The solution is cooled at −78° C., t-butyllithium (1.5 M in pentane; 1.20 ml, 1.80 mmol, 2.00 equivalents) is added dropwise and the mixture is stirred at −78° C. for 30 minutes. ClPC$_6$H$_5$ (238 mg, 1.08 mmol, 1.20 equivalents) is added dropwise at −78° C. to the dark red solution obtained, the solution is stirred at −78° C. for 30 minutes and subsequently stirred at RT for 10 minutes. The reaction mixture is hydrolysed by means of saturated NH$_4$Cl solution (10 ml), TBME (50 ml) is added, the organic phase is separated off and dried over Na$_2$SO$_4$. The solvent is then distilled off on a rotary evaporator and the crude product is purified by column chromatography (10 g of silica gel, n-heptane/TBME 10:1). Compound (A) is obtained as a yellow solid (184 mg, 0.28 mmol, 31%).

$^1$H-NMR (C$_6$D$_6$), selected characteristic signals: 3.97 (s, 5H, Cp), 3.92-3.88 (m, 1H), 3.71-3.68 (m, 1H), 2.87-2.83 (m, 1H); $^{31}$P-NMR (C$_6$D$_6$, 121 MHz): −16.8 (d), −21.6 (d).

EXAMPLE B2

Preparation of (S)-1-diphenylphosphino-2-[α-(S)-hydroxy(o-di((3,5-bis(tri-fluoromethyl)phenyl)phos-phinophenyl)methyl]ferrocene of the formula (B)

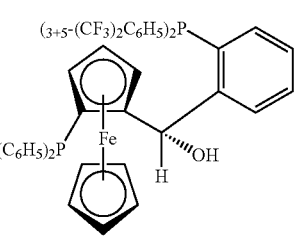

The procedure of Example B1 is repeated using chlorobis(3,5-di(trifluoromethyl)-phenyl)phosphane. Compound B is obtained as a yellow solid.

$^1$H-NMR (C$_6$D$_6$), selected characteristic signals: 4.21-4.20 (m, br, 1H), 3.89-3.84 (m, br, 1H), 3.84 (s, 5H, Cp), 3.74-3.70 (m, br, 1H), 2.95 (s, 1H), 2.71 (s, br, 1H); $^{31}$P-NMR (C$_6$D$_6$, 121 MHz): −13.8 (d), −22.9 (d).

EXAMPLE B3

Preparation of (S)-1-di(3,5-dimethyl-4-methoxyphenyl)phosphino-2-[α-(S)-hydroxy(o-diphenylphosphinophenyl)methyl]ferrocene of the formula (C)

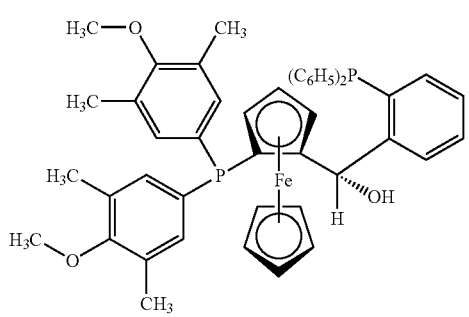

The procedure of Example BI is repeated using compound (2) from Example A2. Compound C is obtained as a yellow solid.

$^1$H-NMR (C$_6$D$_6$), selected characteristic signals: 4.03 (s, 5H, Cp), 3.23 (s; 6H, OCH$_3$), 3.17 (s, 6H, OCH$_3$), 2.26 (s, 6H, CH$_3$), 1.94 (s, 6H, CH$_3$); $^{31}$P-NMR (C$_6$D$_6$, 121 MHz): −16.9 (d), −23.6 (d).

EXAMPLE B4

Preparation of (S)-1-di(3,5-dimethyl-4-methoxyphenyl)phosphino-2-[α-(S)-hydroxy(o-di((3,5-bis(trifluoromethyl)phenyl)phosphinophenyl)methyl]ferrocene of the formula D

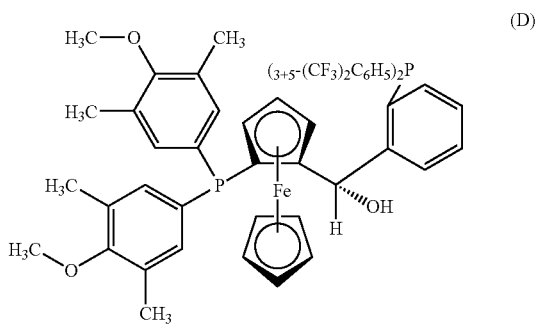

The procedure of Example B1 is repeated using compound (2) from Example A2 and chlorobis(3,5-di(trifluoromethyl)phenyl)phosphane. Compound D is obtained as a yellow solid.

$^1$H-NMR ($C_6D_6$), selected characteristic signals: 3.75 (s, 5H, Cp), 3.21 (s, 6H, $OCH_3$), 3.15 (s, 6H, $OCH_3$), 2.03 (s, 6H, $CH_3$), 1.88 (s, 6H, $CH_3$); $^{31}$P-NMR ($C_6D_6$, 121 MHz): −14.1 (d), −24.7 (d).

C) Preparation of Metal Complexes

General method: In a Schlenk vessel filled with argon, a catalyst solution is prepared by dissolving, for example, 4.73 (0.01265 mmol) of $[Rh(norbornadiene)_2]BF_4$ or another metal complex and 8.96 mg (0.0133 mmol) of diphosphine ligand in 5 ml of degassed methanol.

D) Use Examples

EXAMPLE D1

Hydrogenation of Methyl Trans-Acetamidocinnamate 0.555 g (2.53 mmol) of methyl trans-acetamidocinnamate and 5 ml of degassed methanol are introduced in succession into a Schlenk vessel filled with argon. A catalyst solution consisting of 4.73 g (0.01265 mmol) of $[Rh(norbornadiene)_2]BF_4$, 8.77 mg (0.0133 mmol) of ligand A and 5 ml of degassed methanol is prepared in a second Schlenk vessel filled with argon. This solution and the catalyst solution are then transferred in succession by means of a steel capillary into a 50 ml glass reactor filled with argon. The ratio of substrate/catalyst (s/c) is 200. The reactor is closed and a pressure of 1.05 bar is set by means of 4 flushing cycles (pressurization to 1 bar of hydrogen). The autoclave is thermostated at 25° C. and the reaction is started by switching on the stirrer. The reactor is stirred for 1 hour. After opening the reactor, a reddish reaction solution is isolated. The conversion is quantitative (determined by means of GC and $^1$H-NMR). Removal of the solvent on a rotary evaporator gives a quantitative yield of the methyl ester of (S)—N-acetylphenylalanine having an enantiomeric purity of 99.1% ee (determined by means of GC; column: Chirasil-L-Val.).

Comparison: (S)-1-Diplienylphosphino-2-[α-(S)-methoxy(o-diphenylphosphinophenyl)-methyl]ferrocene (methoxy-TANIAPHOS) is used as a ligand.

A method similar to that of Example D1 is employed. 8.96 mg (0.0133 mmol) of the ligand methoxy-TANIAPHOS are used in place of the ligand A. The conversion is 100%. Removal of the solvent on a rotary evaporator gives a quantitative yield of the methyl ester of (S)—N-acetylphenylalanine having an enantiomeric purity of 99% ee.

EXAMPLE D2

Hydrogenation of Dimethyl Itaconate

A method analogous to that of Example D1 is employed. 0.4 g (2.53 mmol) of dimethyl itaconate is used as starting material, and 8.77 mg (0.0133 mmol) of A are used as ligand. The conversion is 100%. Removal of the solvent on a rotary evaporator gives a quantitative yield of (2R)-dimethyl succinate having an enantiomeric purity of 99.5% ee.

Comparison:

A method similar to that of Example D2 is employed. 8.96 mg (0.0133 mmol) of methoxy-TANIAPHOS are used in place of the ligand A. The conversion is 100%. Removal of the solvent on a rotary evaporator gives a quantitative yield of (2R)-dimethyl succinate having an enantiomeric purity of >99.4% ee.

EXAMPLE D3

Hydrogenation of 2-methylcinnamic acid 0.41 g (2.53 mmol) of 2-methylcinnamic acid and 5 ml of degassed methanol are introduced in succession into a Schlenk vessel filled with argon. A catalyst solution consisting of 4.73 mg (0.01265 mmol) of $[Rh(norbornadiene)_2]BF_4$, 8.77 mg (0.0133 mmol) of ligand A and 5 ml of degassed methanol is prepared in a second Schlenk vessel filled with argon. This solution and the catalyst solution are then transferred in succession by means of a steel capillary into a 50 ml autoclave filled with argon. The ratio of substrate/catalyst is 200. The autoclave is closed and a pressure of 5 bar is set by means of 4 flushing cycles (pressurization to 10 bar of hydrogen). The autoclave is thermostated at 25° C. and the reaction is started by switching on the stirrer. The reactor is stirred for 19 hours. After opening the autoclave, a reddish reaction solution is isolated. The conversion is quantitative (determined by means of GC and $^1$H-NMR). Removal of the solvent on a rotary evaporator gives a quantitative yield of 2-methyl-3-phenylpropionic acid having an enantiomeric purity of 29% ee (determined by means of HPLC after conversion into the methyl ester; column: Chiracel OB.).

Comparison:

A method similar to that of Example D3 is employed. 8.96 mg (0.0133 mmol) of methoxy -TANIAPHOS are used in place of the ligand A. The conversion is 100%. Removal of the solvent on a rotary evaporator gives a quantitative yield of 2-methyl-3-phenylpropionic acid having an enantiomeric purity of 30% ee.

EXAMPLE D4

Hydrogenation of methyl phenylglyoxylate

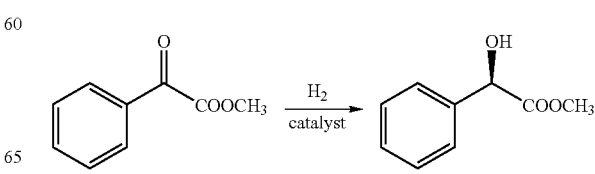

0.415 g (2.53 mmol) of methyl phenylglyoxylate and 5 ml of degassed methanol are introduced in succession into a Schlenk vessel filled with argon. A catalyst solution consisting of 4.73 mg (0.01265 mmol) of [Rh(norbornadiene)$_2$]BF$_4$, 8.77 mg (0.0133 mmol) of ligand A and 5 ml of degassed methanol is prepared in a second Schlenk vessel filled with argon. This solution and the catalyst solution are then transferred in succession by means of a steel capillary into a 50 ml autoclave filled with argon. The ratio of substrate/catalyst is 200. The autoclave is closed and a pressure of 80 bar is set by means of 4 flushing cycles (pressurization to 20 bar of hydrogen). The autoclave is thermostated at 25° C. and the reaction is started by switching on the stirrer. The reactor is stirred for 19 hours. After opening the autoclave, a reddish reaction solution is isolated. The conversion is quantitative (determined by means of GC and $^1$H-NMR). Removal of the solvent on a rotary evaporator gives a quantitative yield of (S)-methyl lactate having an enantiomeric purity of 42% ee (determined by means of HPLC after conversion into the methyl ester; column: Chiracel OJ.).

Comparison:

A method similar to that of Example D4 is employed. 8.96 mg (0.0133 mmol) of methoxy-TANIAPHOS are used in place of the ligand A. The conversion is 100%. Removal of the solvent on a rotary evaporator gives a quantitative yield of (S)-methyl lactate having an enantiomeric purity of only 19% ee.

EXAMPLES D5-D22

Hydrogenation of Various Starting Materials

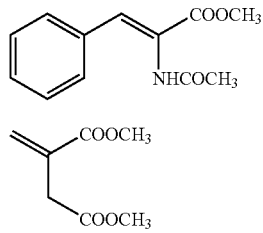

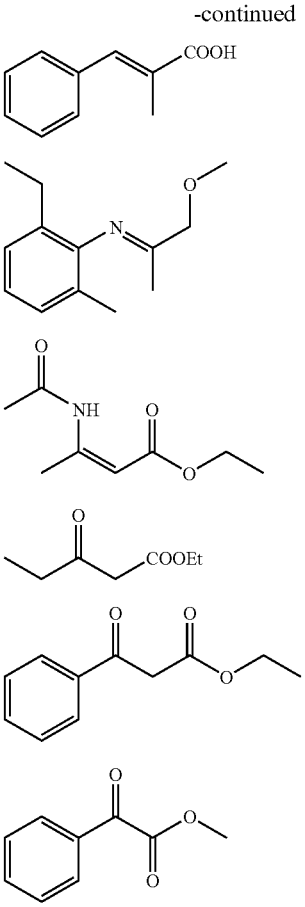

The experimental procedure is similar to that of Example DI. 2.53 mmol of starting material are always used, and the ratio of substrate to catalyst (sic) is always 200. The reaction parameters and the results are summarized in Table I below.

In Examples 5, 11, 16 and 20, toluene (10 ml) is used as solvent. In Examples 6 to 8, 12, 13, 17, 18, 21 and 22, ethanol (10 ml, in Examples 6 and 17 9.5 ml) is used as solvent. In Examples 9, 10, 14, 15 and 19, methanol (10 ml) is used as solvent.

TABLE 1

| Example | Starting material | Metal complex | Ligand | Additives | p(H$_2$) [bar] | Temperature [° C.] | Time [h] | Conversion [%] | e.e. [%] | Configuration |
|---|---|---|---|---|---|---|---|---|---|---|
| 5 | S4 | [Ir(cod)Cl]$_2$ | A | TBAI/TFA | 80 | 25 | 19 | 48 | 67 | R |
| 6 | S5 | [Rh(nbd)$_2$]BF$_4$ | A | TFE | 1 | 25 | 1 | 59.6 | 68.2 | S |
| 7 | S6 | [RuI$_2$(p-cymene)]$_2$ | A | HCl | 80 | 80 | 20 | 100 | 93.4 | S |
| 8 | S7 | [RuI$_2$(p-cymene)]$_2$ | A | HCl | 80 | 80 | 21 | 100 | 98.4 | R |
| 9 | S1 | [Rh(nbd)$_2$]BF$_4$ | B |  | 1 | 25 | 1 | 100 | 97.2 | S |
| 10 | S3 | [Rh(nbd)$_2$]BF$_4$ | B |  | 5 | 25 | 19 | 75 | 87.2 | 2 |
| 11 | S8 | [Rh(nbd)Cl]$_2$ | B |  | 80 | 25 | 20 | 88.5 | 59.2 | R |
| 12 | S6 | [RuI$_2$(p-cymene)]$_2$ | B | HCl | 80 | 80 | 21 | 100 | 98.2 | S |
| 13 | S7 | [RuI$_2$(p-cymene)]$_2$ | B | HCl | 80 | 80 | 20 | 100 | 91.8 | S |
| 14 | S1 | [Rh(nbd)$_2$]BF$_4$ | C |  | 1 | 25 | 1 | 100 | 98.4 | S |
| 15 | S2 | [Rh(nbd)$_2$]BF$_4$ | C |  | 1 | 25 | 1 | 100 | 99.4 | R |
| 16 | S4 | [Ir(cod)Cl]$_2$ | C | TBAI/TFA | 80 | 25 | 16 | 50 | 59 | R |
| 17 | S5 | [Rh(nbd)$_2$]BF$_4$ | C | TFE | 1 | 25 | 1 | 98.8 | 80.4 | S |
| 18 | S6 | [RuI$_2$(p-cymene)]$_2$ | C | HCl | 80 | 80 | 15 | 100 | 95.6 | S |
| 19 | S1 | [Rh(nbd)$_2$]BF$_4$ | D |  | 1 | 25 | 1 | 100 | 99.5 | S |
| 20 | S4 | [Ir(cod)Cl]$_2$ | D | TBAI/TFA | 80 | 25 | 15.5 | 100 | 52 | R |

TABLE 1-continued

| Example | Starting material | Metal complex | Ligand | Additives | p(H$_2$) [bar] | Temperature [° C.] | Time [h] | Conversion [%] | e.e. [%] | Configuration |
|---|---|---|---|---|---|---|---|---|---|---|
| 21 | S6 | [RuI$_2$(p-cymene)]$_2$ | D | HCl | 80 | 80 | 16.5 | 98 | 98.6 | S |
| 22 | S7 | [RuI$_2$(p-cymene)]$_2$ | D | HCl | 80 | 80 | 16 | 100 | 92.9 | S |

*): TFE: 0.5 ml of 3,3,3-trifluoroethanol; TBAI: tetrabutylammonium iodide (TBAI to iridium is 2); TFA: 30 μl of trifluoroacetic acid; HCl: 60 μl of 1N aqueous HCl The invention is claimed:

1. A compound of the formula I or I',

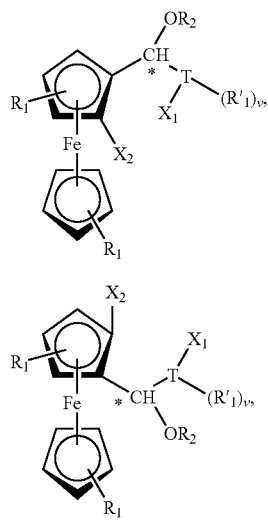

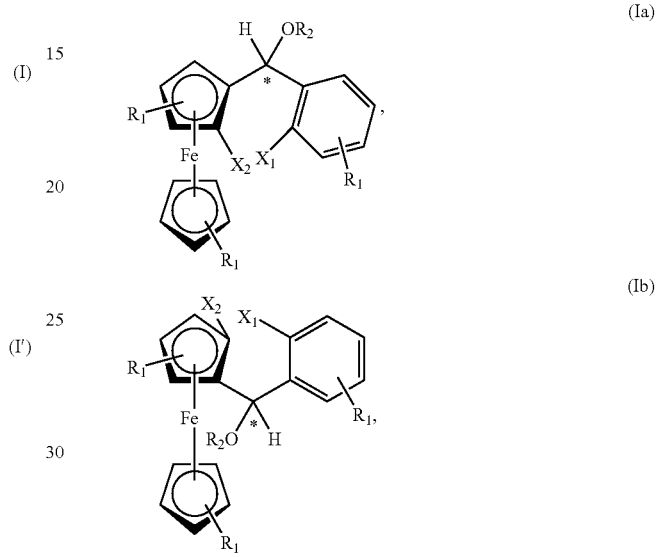

where both $R_1$ independently are a hydrogen atom or $C_1$-$C_4$-alkyl and $R'_1$ is $C_1$-$C_4$-alkyl;

$X_1$ and $X_2$ are each, independently of one another, a secondary phosphine group;

$R_2$ is hydrogen, $R_{01}R_{02}R_{03}Si$—, $C_1$-$C_{18}$-acyl substituted by halogen, hydroxy, $C_1$-$C_8$-alkoxy or $R_{04}R_{05}N$—, or $R_{06}$-$X_{01}$—C(O)—;

$R_{01}$, $R_{02}$ and $R_{03}$ are each, independently of one another, $C_1$-$C_{12}$-alkyl, unsubstituted or $C_1$-$C_4$-alkyl- or $C_1$-$C_4$-alkoxy-substituted $C_6$-$C_{10}$-aryl or $C_7$-$C_{12}$-aralkyl;

$R_{04}$ and $R_{05}$ are each, independently of one another, hydrogen, $C_1$-$C_{12}$-alkyl, $C_3$-$C_8$-cycloalkyl, $C_6$-$C_{10}$-aryl or $C_7$-$C_{12}$-aralkyl, or $R_{04}$ and $R_{05}$ together are trimethylene, tetramethylene, pentamethylene or 3-oxapentylene;

$R_{06}$ is $C_1$-$C_{18}$-alkyl, unsubstituted or $C_1$-$C_4$-alkyl- or $C_1$-$C_4$-alkoxy-substituted $C_3$-$C_8$-cycloalkyl, $C_6$-$C_{10}$-aryl or $C_7$-$C_{12}$-aralkyl;

$X_{01}$ is —O— or —NH—;

T is $C_6$-$C_{20}$-arylene;

v is 0 or an integer from 1 to 4; $X_1$ is bound in the ortho position relative to the T-C* bond; and

* denotes a mixture of racemic or enantiomerically pure diastereomers or pure racemic or enantiomerically pure diastereomers.

2. The compound according to claim 1, which corresponds to the formula Ia or Ib, where $R_1$, $X_1$, $X_2$ and $R_2$ and also * have the meanings indicated in claim 1.

3. The compound according to claim 1, wherein $R_1$ is a hydrogen atom.

4. The compound according to claim 1, wherein an alkyl group $R_{01}$, $R_{02}$ or $R_3$ has from 1 to 8 carbon atoms, an aryl group $R_{01}$, $R_{02}$ or $R_{03}$ is phenyl or naphthyl and an aralkyl group $R_{01}$, $R_{02}$ or $R_{03}$ is benzyl or phenylethyl.

5. The compound according to claim 1, wherein $R_{04}$ and $R_{05}$ are each, independently of one another, hydrogen, $C_1$-$C_4$-alkyl, $C_5$-$C_6$-cycloalkyl, phenyl or benzyl, or $R_{04}$ and $R_{05}$ together are tetramethylene, pentamethylene or 3-oxapentyl-1,5-ene.

6. The compound according to claim 1, wherein an acyl group $R_2$ is derived from a carboxylic acid.

7. The compound according to claim 1, wherein an alkyl group $R_{06}$ has from 1 to 12 carbon atoms, a cycloalkyl group $R_{06}$ is cyclopentyl or cyclohexyl, an aryl group $R_{06}$ is naphthyl or phenyl and an aralkyl group $R_{06}$ is phenylethyl or benzyl.

8. The compound according to claim 1, wherein the secondary-phosphine groups $X_1$ and $X_2$ each contain two identical hydrocarbon radicals.

9. The compound according to claim 1, wherein the secondary phosphine groups $X_1$ and $X_2$ are identical or different.

10. The compound according to claim 1, wherein the secondary-phosphine groups $X_1$ and $X_2$ contain hydrocarbon radicals which have from 1 to 22 carbon atoms, are unsubstituted or substituted and/or contain heteroatoms selected from the group consisting of O, S and N($C_1$-$C_4$-alkyl).

11. The compound according to claim 10, wherein the secondary phosphine contains two identical or different hydrocarbon radicals selected from the group consisting of linear or branched $C_1$-$C_{12}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$-; phenyl, naphthyl, furyl or benzyl; and phenyl or benzyl substituted by halogen, $C_1$-$C_6$-alkyl, $C_1$-$C_6$-haloalkyl, $C_1$-$C_6$-alkoxy, $C_1$-$C_6$-haloalkoxy, $(C_6H_5)_3$Si, $(C_1$-$C_{12}$-alkyl$)_3$Si, secondary amino or —$C_{02}$-$C_1$—$C_6$-alkyl.

12. The compound according to claim 1, wherein the secondary-phosphino group corresponds to the formula —$PR_3R_4$, where $R_3$ and $R_4$ are each, independently of one another, a hydrocarbon radical which has from 1 to 18 carbon atoms and may be unsubstituted or substituted by halogen, $C_1$-$C_6$-alkyl, $C_1$-$C_6$-haloalkyl, $C_1$-$C_6$-alkoxy, $C_1$-$C_6$-haloalkoxy, $(C_1$-$C_4$-alkyl$)_2$amino, $(C_6H_5)_3$Si, $C_1$-$C_{12}$-alkyl$)_3$Si or —$CO_{02}$-$C_1$—$C_6$-alkyl and/or contains heteroatoms O.

13. The compound according to claim 1, wherein the secondary-phosphine groups $X_1$ and $X_2$ are cyclic secondary phosphino.

14. The compound according to claim 1, wherein the cyclic secondary phosphino corresponds to one of the formulae

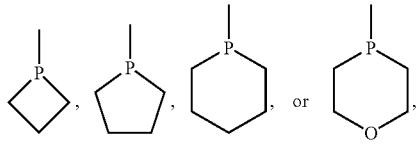

where the rings are unsubstituted or monosubstituted or polysubstituted by —OH, $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkylphenyl or $C_1$-$C_4$-alkoxyphenyl, benzyl, $C_1$-$C_4$-alkylbenzyl or $C_1$-$C_4$-alkoxybenzyl, benzyloxy, $C_1$-$C_4$-alkylbenzyloxy or $C_1$-$C_4$-alkoxybenzyloxy or $C_1$-$C_4$-alkylidenedioxyl.

15. The compound according to claim 1, which corresponds to a diastereomer of the formula Ic, Id, Ie or If,

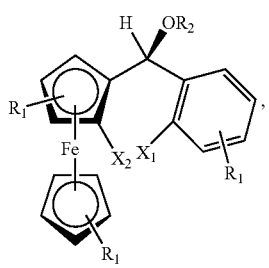

(Ic)

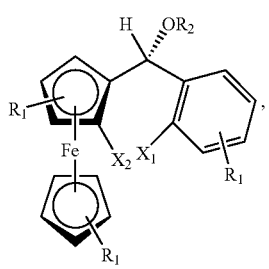

(Id)

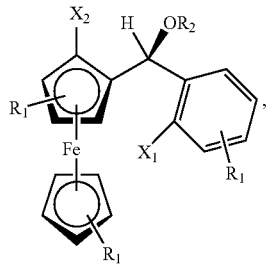

(Ie)

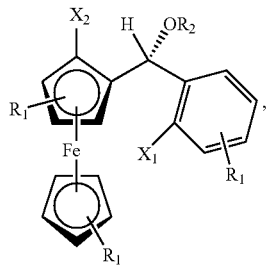

(If)

where
$R_1$ is hydrogen and $R_2$, $X_1$ and $X_2$ have the meanings indicated in claim 1.

16. The compound according to claim 15, wherein $X_1$ and $X_2$ in the formulae Ic, Id, Ie and If are identical or different acyclic secondary phosphine selected from the group consisting of —$P(C_1$-$C_6$-alkyl$)_2$, —$P(C_5$-$C_8$-cycloalkyl$)_2$, —$P(C_7$-$C_8$-bicycloalkyl$)_2$, —$P(C_5$-$C_8$-cycloalkyl$)_2$, —$P(o$-furyl$)_2$, —$P(C_6H_5)_2$, —$P[2$-$(C_1$-$C_6$-alkyl$)C_6H_4]_2$, —$P[3$-$(C_1$-$C_6$-alkyl$)C_6H_4]_2$, —$P[4$-$(C_1$-$C_6$-alkyl$)C_6H_4]_2$, —$P[2$-$(C_1$-$C_6$-alkoxy$)C_6H_4]_2$, —$P[3$-$(C_1$-$C_6$-alkoxy$)C_6H_4]_2$, —$P[4$-$(C_1$-$C_6$-alkoxy$)C_6H_4]_2$, —$P[2$-$(trifluoromethyl$)C_6H_4]_2$, —$P[3$-$(trifluoromethyl)$ $C_6H_4]_2$, —$P[4$-$(trifluoromethyl$)C_6H_4]_2$, —$P[3,5$-bis(trifluoromethyl$)C_6H_3]_2$, —$P[3,5$-bis($C_1$-$C_6$-alkyl$)_2C_6H_3]_2$, —$P[3,5$-bis($C_1$-$C_6$-alkoxy$)_2C_6H_3]_2$ and —$P[3,5$-bis($C_1$-$C_6$-alkyl$)_2$-$_4$-$(C_1$-$C_6$-alkoxy$)C_6H_2]_2$, or identical or different cyclic phosphine selected from the group consisting of

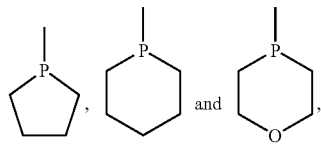

where the rings are unsubstituted or monosubstituted or polysubstituted by HO, $C_1$-$C_4$-alkyl, $C_1$-$C_4$-alkoxy, $C_1$-$C_4$-alkoxy-$C_1$-$C_2$-alkyl, phenyl, benzyl, benzyloxy or $C_1$-$C_4$-alkylidenedioxyl.

17. The compound according to claim 15, wherein secondary phosphino groups $X_1$ and $X_2$ are —$P(CH_3)_2$, —$P(i$-$C_3H_7)_2$, —$P(n$-$C_4H_9)_2$, —$P(i$-$C_4H_9)_2$, —$P(C_6H_{11})_2$, —$P(norbornyl)_2$, —$P(o$-furyl$)_2$, —$P(C_6H_5)_2$, P[2-(methyl)$C_6H_4]_2$, P[3-(methyl) $C_6$-$H_4]_2$, —P [4-(methyl)$C_6H_4]_2$, —$P[4$-(methoxy)$C_6H_4]_2$, —$P[3$-(methoxy)$C_6H_4]_2$, —$P[4$-methoxy)$C_6H_4]_2$, —$P[3$-(trifluoromethyl)$C_6H_4]_2$, —$P[4$-(trifluoromethyl)$C_6H_4]_2$, —P[3,5-bis(trifluoromethyl) $C_6H_3]_2$, —$P[3,5$-bis(methyl$)_2C_6H_3]_2$, —$P[3,5$-bis(methoxy$)_2C_6H_3]_2$ and —$P[3,5$-bis(methyl$)_2$-4-(methoxy)$C_6H_2]_2$, or a group of the formula where
R' is methyl, ethyl, methoxy, ethoxy, phenoxy, benzyloxy, methoxymethyl, ethoxymethyl or benzyloxymethyl and R" has the same meanings as R'.

18. A compound of the formula F or F', (F)

(F')

where
$X_2$, T, $R_1$, $R'_1$ and v have the meanings given in claim 1, $R_2$ is H and $X_4$ is Cl, Br or I.

19. A metal complex of a metal selected from the group consisting of Cu, Ag, Au, Ni, Co, Rh, Pd, Ir, Ru and Pt with a compound of the formula I or I' according to claim 1 as ligand.

20. The metal complex according to claim 19, wherein the metal is rhodium, iridium or ruthenium.

21. The metal complex according to claim 19, which corresponds to the formula II or III $$A_1 MeL_n \qquad (II),$$

$$(A_1 MeL_n)^{(z+)}(E^-)_z \qquad (III),$$

where $A_1$ is one of the compounds of the formula I or I', L represents identical or different monodentate, anionic or nonionic ligands or L represents identical or different bidentate, anionic or nonionic ligands;
n is 2, 3 or 4 when L is a monodentate ligand, or n is 1 or 2 when L is a bidentate ligand;
z is 1, 2 or 3;
Me is a metal selected from the group consisting of Rh, Ir and Ru; with the metal having the oxidation state 0, 1, 2, 3 or 4;
$E^-$ is the anion of an oxo acid or a complex acid; and
the anionic ligands balance the charge of the oxidation state 1, 2, 3 or 4 of the metal.

22. The metal complex according to claim 20, which corresponds to the formula IV or V, $$[A_1 Me_2 YZ] \qquad (IV),$$

$$[A_1 Me_2 Y]^{30} E_1^- \qquad (V),$$

where
$A_1$ is one of the compounds of the formula I or I';
$Me_2$ is rhodium or iridium;
Y represents two olefins or a diene;
Z is Cl, Br or I; and
$E_1^-$ is the anion of an oxo acid or complex acid.

23. A process for preparing a chiral organic compound by asymmetric addition of hydrogen onto a carbon-carbon or carbon-heteroatom double bond in a prochiral organic compound in the presence of a catalyst, wherein the addition reaction is carried out in the presence of a catalytic amount of at least one metal complex according to claim 19.

24. The metal complex according to claim 19, wherein the compound is selected from the group consisting of compounds of the formulae Ia to If, (Ia)

(Ib)

where
both $R_1$ independently are a hydrogen atom or $C_1$-$C_4$-alkyl;
$X_1$ and $X_2$ are each, independently of one another, a secondary phosphine group;
$R_2$ is hydrogen, $R_{01}R_{02}R_{03}Si$—, $C_1$-$C_{18}$-acyl substituted by halogen, hydroxy, $C_1$-$C_8$-alkoxy or $R_{04}R_{05}N$—, or $R_{06}$—$X_{01}$—C(O)—;

$R_{01}$, $R_{02}$ and $R_{03}$ are each, independently of one another, $C_1$-$C_{12}$-alkyl, unsubstituted or $C_1$-$C_4$-alkyl- or $C_1$-$C_4$-alkoxy-substituted $C_6$-$C_{10}$-aryl or $C_7$-$C_{12}$-aralkyl;

$R_{04}$ and $R_{05}$ are each, independently of one another, hydrogen, $C_1$-$C_{12}$-alkyl, $C_3$-$C_8$-cycloalkyl, $C_6$-$C_{10}$-aryl or $C_7$-$C_{12}$-aralkyl, or $R_{04}$ and $R_{05}$ together are trimethylene, tetramethylene, pentamethylene or 3-oxapentylene;

$R_{06}$ is $C_1$-$C_{18}$-alkyl, unsubstituted or $C_1$-$C_4$-alkyl- or $C_1$-$C_4$-alkoxy-substituted $C_3$-$C_8$-cycloalkyl, $C_6$-$C_{10}$-aryl or $C_7$-$C_{12}$-aralkyl;

$X_{01}$ is —O— or —NH—;

$X_1$ is bound in the ortho position relative to the T-C* bond; and

* denotes a mixture of racemic or enantiomerically pure diastereomers or pure racemic or enantiomerically pure diastereomers,

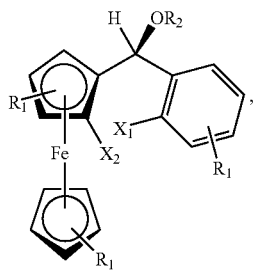

(Ic)

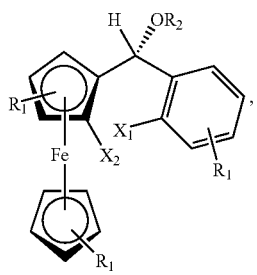

(Id)

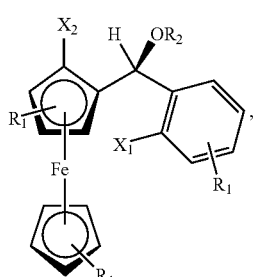

(Ie)

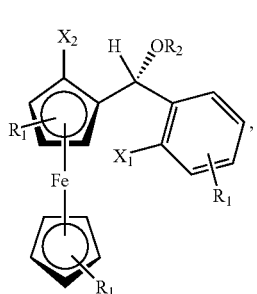

(If)

where $R_1$ is hydrogen and $R_2$, $X_1$ and $X_2$ have the meanings indicated above for formulae Ia and Ib.

25. The metal complex according to claim 24, wherein the metal is rhodium, iridium or ruthenium.

26. The metal complex according to claim 24, which corresponds to the formula II or III $$A_1MeL_n \quad (II),$$

$$(A_1MeL_n)^{(z+)}(E^-)_z \quad (III),$$

where $A_1$ is one of the compounds of the formula I or I',

L represents identical or different monodentate, anionic or nonionic ligands or L represents identical or different bidentate, anionic or nonionic ligands;

n is 2, 3 or 4 when L is a monodentate ligand, or n is 1 or 2 when L is a bidentate ligand;

z is 1, 2 or 3;

Me is a metal selected from the group consisting of Rh, Ir and Ru; with the metal having the oxidation state 0, 1, 2, 3 or 4;

$E^-$ is the anion of an oxo acid or a complex acid; and the anionic ligands balance the charge of the oxidation state 1, 2, 3 or 4 of the metal.

27. A process for preparing a chiral organic compound by asymmetric addition of hydrogen onto a carbon-carbon or carbon-heteroatom double bond in aprochiral organic compound in the presence of a catalyst, wherein the addition reaction is carried out in the presence of a catalytic amount of at least one metal complex according to claim 24.

28. A compound of one of the formulae F1 to F6,

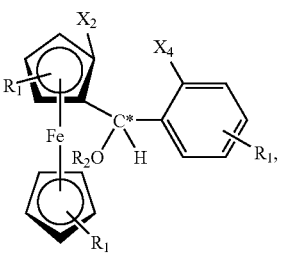

(F1)

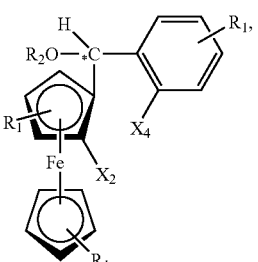

(F2)

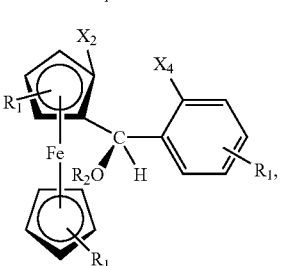

(F3)

-continued

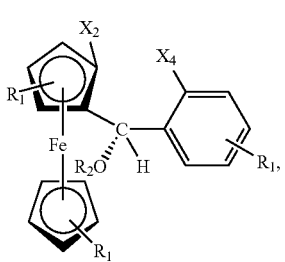
(F4)

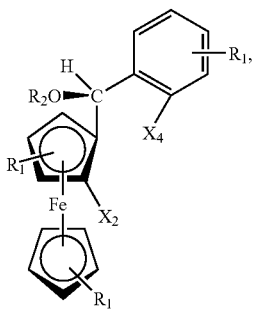
(F5)

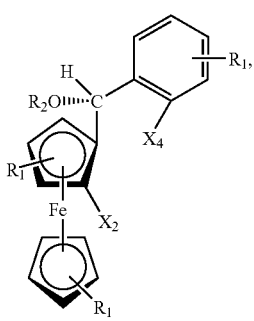
(F6)

where
X$_2$ and R$_1$ have the meanings given in claim 1, R$_2$ is H and X$_4$ is Cl, Br or I.

29. The metal complex according to claim 21, wherein A$_1$ is one of the compounds of formulae Ia to If,

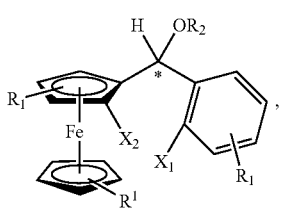
(Ia)

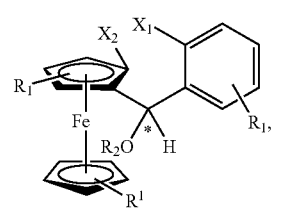
(Ib)

where
both R$_1$ independently are a hydrogen atom or C$_1$-C$_4$-alkyl;
X$_1$ and X$_2$ are each, independently of one another, a secondary phosphine group;

R$_2$ is hydrogen, R$_{01}$R$_{02}$R$_{03}$Si—, C$_1$-C$_{18}$-acyl substituted by halogen, hydroxy, C$_1$-C$_8$-alkoxy or R$_{04}$R$_{05}$N—, or R$_{06}$—X$_{01}$—C(O)—;

R$_{01}$, R$_{02}$ and R$_{03}$ are each, independently of one another, C$_1$-C$_{12}$-alkyl, unsubstituted or alkyl- or C$_1$-C$_4$-alkoxy-substituted C$_6$-C$_{10}$-aryl or C$_7$-C$_{12}$-aralkyl;

R$_{04}$ and R$_{05}$ are each, independently of one another, hydrogen, C$_1$-C$_{12}$-alkyl, C$_3$-C$_8$-cycloalkyl, C$_6$-C$_{10}$-aryl or C$_7$-C$_{12}$-aralkyl, or R$_{04}$ and R$_{05}$ together are trimethylene, tetramethylene, pentamethylene or 3-oxapentylene;

R$_{06}$ is C$_1$-C$_{18}$-alkyl, unsubstituted or C$_1$-C$_4$-alkyl- or C$_1$-C$_4$-alkoxy-substituted C$_3$-C$_8$-cycloalkyl, C$_6$-C$_{10}$-aryl or C$_7$-C$_{12}$-aralkyl;

X$_{10}$ is —O— or —NH—;

X$_1$ is bound in the ortho position relative to the T-C* bond; and

* denotes a mixture of racemic or enantiomerically pure diastereomers or pure racemic or enantiomerically pure diastereomers,

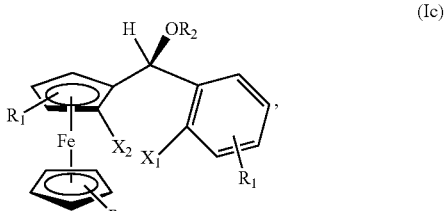
(Ic)

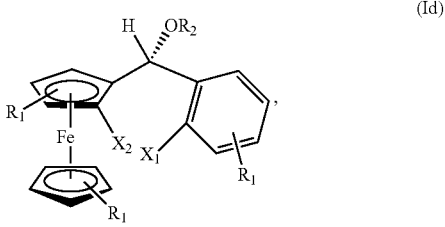
(Id)

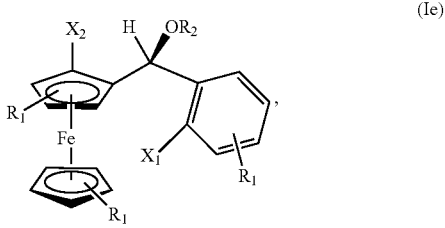
(Ie)

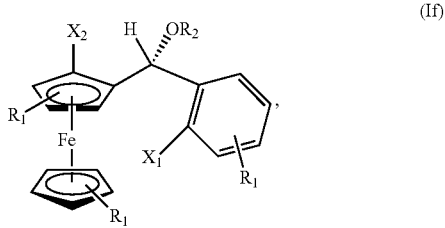
(If)

where
R$_1$ is hydrogen and R$_2$, X$_1$ and X$_2$ have the meanings indicated above for formulae Ia and Ib.

30. The metal complex according to claim 22, wherein $A_1$ is one of the compounds of formula Ia or Ib,

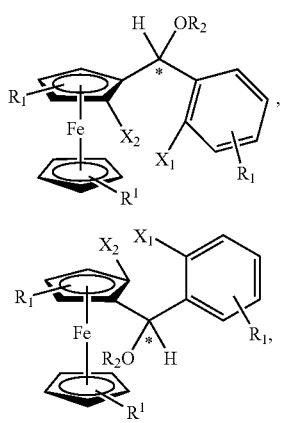

where
- both $R_1$ independently are a hydrogen atom or $C_1$-$C_4$-alkyl;
- $X_1$ and $X_2$ are each, independently of one another, a secondary phosphine group;
- $R_2$ is hydrogen, $R_{01}R_{02}R_{03}Si$—, $C_1$-$C_{18}$-acyl substituted by halogen, hydroxy, $C_1$-$C_8$-alkoxy or $R_{04}R_{05}N$—, or $R_{06}$-$X_{01}$—C(O)—;
- $R_{01}$, $R_{02}$ and $R_{03}$ are each, independently of one another, $C_1$-$C_{12}$-alkyl, unsubstituted or $C_1$-$C_4$-alkyl- or $C_1$-$C_4$-alkoxy-substituted $C_6$-$C_{10}$-aryl or $C_7$-$C_{12}$-aralkyl;
- $R_{04}$ and $R_{05}$ are each, independently of one another, hydrogen, $C_1$-$C_{12}$-alkyl, $C_3$-$C_8$-cycloalkyl, $C_6$-$C_{10}$-aryl or $C_7$-$C_{12}$-aralkyl, or $R_{04}$ and $R_{05}$ together are trimethylene, tetramethylene, pentamethylene or 3-oxapentylene;
- $R_{06}$ is $C_1$-$C_{18}$-alkyl, unsubstituted or $C_1$-$C_4$-alkyl- or $C_1$-$C_4$-alkoxy-substituted $C_3$-$C_8$-cycloalkyl, $C_6$-$C_{10}$-aryl or $C_7$-$C_{12}$-aralkyl;
- $X_{01}$ is —O— or —NH—;
- $X_1$ is bound in the ortho position relative to the T-C* bond; and
- \* denotes a mixture of racemic or enantiomerically pure diastereomers or pure racemic or enantiomerically pure diastereomers.

31. The metal complex according to claim 26, wherein $A_1$ is one of the compounds of formulae Ia to If,

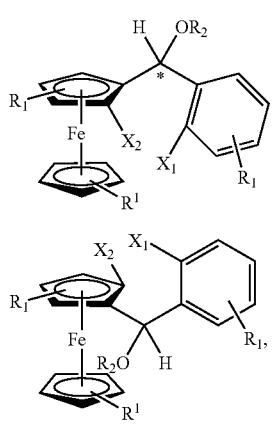

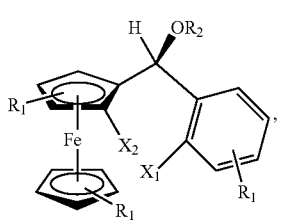

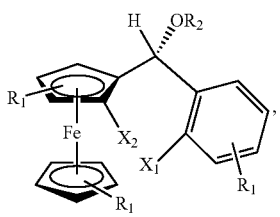

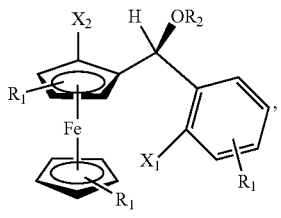

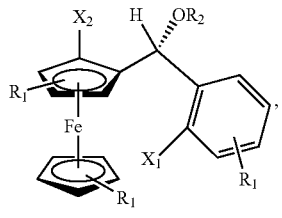

where
$R_1$ is hydrogen and $R_2$, $X_1$ and $X_2$ have the meanings indicated above for formulae Ia and Ib.

* * * * *